(12) United States Patent
Powers et al.

(10) Patent No.: US 7,429,560 B2
(45) Date of Patent: Sep. 30, 2008

(54) KETOAMIDE INHIBITORS IN CHRONIC NERVE DISEASE

(75) Inventors: James C. Powers, Atlanta, GA (US); Jonathan D. Glass, Atlanta, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 386 days.

(21) Appl. No.: 10/671,360

(22) Filed: Sep. 25, 2003

(65) Prior Publication Data

US 2004/0127427 A1 Jul. 1, 2004

Related U.S. Application Data

(60) Provisional application No. 60/413,506, filed on Sep. 25, 2002.

(51) Int. Cl.
*A61K 38/05* (2006.01)
(52) U.S. Cl. .......................................... 514/2; 530/300
(58) Field of Classification Search ...................... None
See application file for complete search history.

(56) References Cited

U.S. PATENT DOCUMENTS

| | | | | |
|---|---|---|---|---|
| 5,514,694 | A | 5/1996 | Powers et al. | 514/357 |
| 5,554,767 | A | 9/1996 | Want et al. | |
| 5,610,297 | A | 3/1997 | Powers | 544/168 |
| 5,650,508 | A | 7/1997 | Powers | 544/168 |
| 5,760,048 | A | 6/1998 | Wang et al. | |
| 6,235,929 | B1 | 5/2001 | Powers | 562/450 |

OTHER PUBLICATIONS

Molla A., et al., "Inhibition of proteolytic activity of poliovirus and rhinovirus 2A proteinases by elastase-specific inhibitors," Aug. 1993 J Virology 67(8): 4688-4695.*
Wang et al. "Pathogenesis of axonal degeneration: parallels between Wallerian degeneration and vincristine neuropathy." J Neuropathol Exp Neurol., 2000, 59(7), 599-606.*
Schaecher et al. "Mechanism of myelin breakdown in experimental demyelination: a putative role for calpain." Neurochem. Res., 2001, 26, 731-737.*
Dourdin et al. *Reduced Cell Migration and Disruption of the Actin Cytoskeleton in Calpain-deficient Embryonic Fibroblasts.* The Journal of Biological Chemistry, Dec. 21, 2001, vol. 276, No. 51, pp. 48382-48388.
Kohli et al. *Calpain is a mediator of preservation-reperfusion injury in rat liver transplantation.* Proc. Natl. Acad. Sci. USA, Medical Sciences, Aug. 1997, vol. 94, pp. 9354-9359.
Kupina et al. *The Novel Calpain Inhibitor SJA6017 Improves Functional Outcome after Delayed Administration in a Mouse Model of Diffuse Brain Injury.* Journal of Neurotrauma, 2001, vol. 18, No. 11, pp. 1229-1240.
Markgraf et al. *Six-hour Window of Opportunity for Calpain Inhibition in Focal Cerebral Ischemia in Rats.* American Heart Association, Inc., 1998, pp. 152-158.
Saatman et al. *Calpain inhibitor AK295 attenuates motor and cognitive deficits following experimental brain injury in the rat.* Proc. Natl. Acad. Sci. USA, Neurobiology, Apr. 1996, vol. 93, pp. 3428-3433.
Schumacher et al. *Pretreatment with Calpain Inhibitor CEP-4143 Inhibits Calpain I Activiation and Cytoskeletal Degradation, Improves Neurological Function, and Enhances Axonal Survival After Traumatic Spinal Cord Injury.* Journal of Neurochemistry, vol. 74, No. 4, pp. 1646-1655, 2000.
Shields et al. *A punative mechanism of demyelination in multiple sclerosis by a proteolytic enzyme, calpain.* Proc. Natl. Acad. Sci. USA, Sep. 1999, vol. 96, pp. 11486-11491.

* cited by examiner

*Primary Examiner*—Cecilia Tsang
*Assistant Examiner*—Christina Marchetti Brad
(74) *Attorney, Agent, or Firm*—Ballard Spahr Andrews & Ingersoll, LLP

(57) ABSTRACT

Compositions and methods for treating neural pathologies are provided. In particular, compositions and methods for treating neural pathologies including axonal degeneration are provided. The compositions include peptide α-ketomides optionally in combination with a second therapeutic agent. Another aspect of the invention provides compositions and methods for treating hyperproliferative disorders. Exemplary compositions for treating hyperproliferative disorders include an anti-proliferative agent such as paclitaxel, in combination with a calpain inhibitor such as AK295.

6 Claims, 13 Drawing Sheets

A

B

KETOAMIDE INHIBITORS IN CHRONIC NERVE DISEASE

CROSS-REFERENCE TO RELATED APPLICATION

This application claims priority to U.S. Provisional Patent Application No. 60/413,506 filed on Sep. 25, 2002, which is incorporated herein in its entirety.

STATEMENT REGARDING FEDERALLY SPONSORED RESEARCH OR DEVELOPMENT

Aspects of the work described herein were supported by Public Health Services grant Nos. 1 R01 GM61964 and 5 P01 NS40405-03 from the National Institutes of Health. Therefore, the U.S. government has certain rights in the invention.

BACKGROUND OF THE INVENTION

1. Field of the Invention

This invention relates generally to the use of calpain inhibitors, in particular to methods for the treatment of peripheral axonal degeneration. Other aspects of the invention relate to the use of peptide α-ketoamide compounds to treat pathological conditions including neural pathologies, and combinations of anti-hyperproliferative agents with peptide α-ketoamides for the treatment of hyperproliferative conditions.

2. Related Art

Peripheral neuropathy is a major dose-limiting complication of commonly used anti-cancer agents, including vincristine, cisplatin, and paclitaxel (Taxol®). Paclitaxel, a microtubule toxin derived from the western yew tree, is particularly effective against solid tumors, but causes a predominantly sensory neuropathy that may be severe enough to necessitate cessation of treatment. The neuropathy is characterized by degeneration of sensory axons, manifesting clinically as numbness, pain, and loss of balance [Lipton, R. B., S. C. Apfel, J. P. Dutcher, R. Rosenberg, J. Kaplan, A. Berger, A. I. Einzig, P. Wiernik and H. H. Schaumburg (1989). "Taxol produces a predominantly sensory neuropathy." *Neurology* 39 (3): 368-73]. Paclitaxel causes a similar sensory neuropathy in rodents that provides a useful experimental model for the treatment of peripheral neuropathies.

Calpains are ubiquitous cytosolic proteolytic enzymes involved in both physiological and pathological cellular functions. They are calcium-dependent enzymes belonging to the family of cysteine proteases. Limited activation of calpains results in modification or activation of protein receptors, enzymes, and cytoskeletal proteins. Pathological cellular insults lead to more generalized calpain activation, resulting in cytoskeletal degradation and cell death.

Calpain activation likely occurs due to sustained elevation of intracellular calcium that is a common feature of models of neuronal injury [Bartus, R. (1997). "The calpain hypothesis of neurodegeneration: evidence for a common cytotoxic pathway." *Neuroscientist* 3: 314-327]. Thus, there is a need for compositions and methods of treating pathologies related to calpain activation.

Because neuronal pathologies, in particular neuropathy, can have a dramatic impact on quality of life of patients, there is also a need for compositions and methods for treating these disorders, in particular, compositions and methods for treating pathologies with little or reduced side effects such as neuropathy.

There is still another need for methods and compositions for treating axonal degeneration.

SUMMARY OF THE INVENTION

Aspects of the present invention are directed to compositions containing calpain inhibitors, preferably peptide α-ketoamides, and methods of their use for the treatment of a pathology, for example pathologies of the peripheral nervous system such as neuropathy, axonal degeneration, or calcium-induced cell injury. It has been discovered that the systemic administration of the peptide α-ketoamides, including for example AK295, is an effective treatment for calpain related pathologies, in particular, axonal degeneration and peripheral neuropathy.

Another aspect of invention provides pharmaceutical compositions for the treatment of hyperproliferative disorders including an anti-hyperproliferative agent, for example a microtubule stabilizing agent for the treatment of the hyperproliferative disorder, in combination with a calpain inhibitor such as a peptide α-ketoamide to limit or reduce side effects of the anti-hyperproliferative agent such as peripheral neuropathy or cytoskeletal degeneration of sensory neurons. Exemplary anti-hyperproliferative agents include microtubule stabilizing agents such as paclitaxel, also referred to as Taxol®. Exemplary calpain inhibitors include peptide α-ketoamides, for example peptide α-ketoamides of formula I.

Additional aspects of the invention are directed to methods for the prevention of behavioral, electrophysiological, and pathological effects of microtubule stabilizing agents by administering a peptide α-ketoamide to a host, for example to a host having microtubule-stabilizing-agent-induced behavioral, electrophysiological, and pathological effects. The structure of an exemplary peptide α-keto amide, AK295, is shown below.

AK295

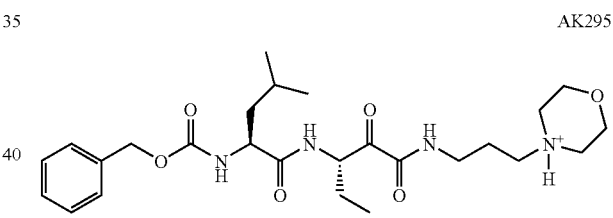

Pathologies including but not limited to paclitaxel-induced axonal degeneration can be treated by administering a peptide α-ketoamide to a host either alone, or in combination with other therapeutic agents, for example anti-inflammatory agents, or anti-hyperproliferative agents.

BRIEF DESCRIPTION OF THE FIGURES

FIG. 9A shows mean blood glucose levels (normal 100 mg/dl). Diabetic animals did not gain weight, and there was no effect on weight of AK295 (bottom graph).

DETAILED DESCRIPTION OF THE INVENTION

Figure 1:
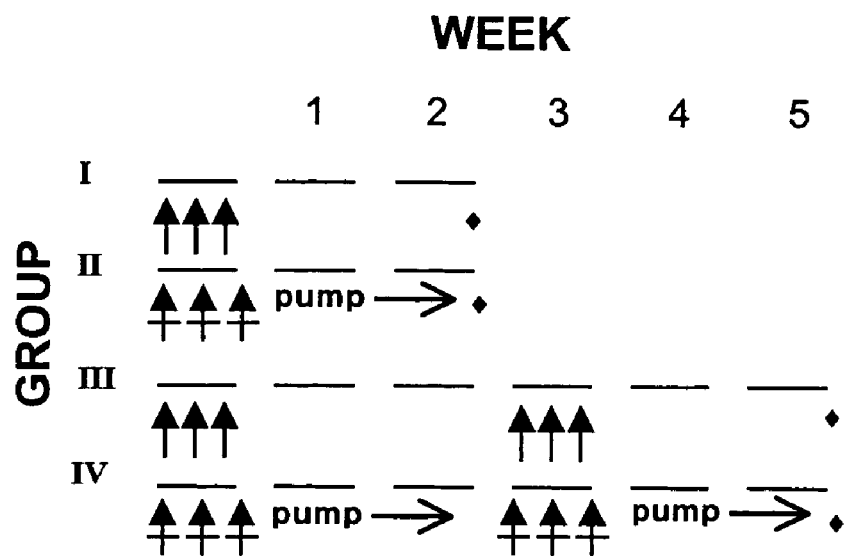
FIG. 1 is a diagram showing an exemplary injection schedule of paclitaxel and AK295.

The present invention may be understood more readily by reference to the following detailed description of the invention and the Examples included therein.

Before the present compounds, compositions and methods are disclosed and described, it is to be understood that this invention is not limited to specific pharmaceutical carriers, or to particular pharmaceutical formulations or administration regimens, as such may, of course, vary. It is also to be understood that the terminology used herein is for the purpose of describing particular embodiments only and is not intended to be limiting.

The peptide α-ketoamides are abbreviated as $M^1$-$AA^2$-$AA^1$-CO—$NR_3R_4$. The keto amide portion of the molecule, -$AA^1$-CO—$NR_3R_4$, is equivalent to —NH-CHRCO—CO—$NR_3R_4$ where the R is the side chain of $AA^1$. Thus the peptide α-ketoamide AK295 is abbreviated as Z-Leu-Abu-CONH—$(CH_2)_3$-4-morpholinyl (AK295). The Z is a benzyloxycarbonyl group, Leu is a leucine residue, Abu is an α-aminobutanoic acid residue, the ketone carbonyl group is part of the Abu residue, CONH is the amide of the α-ketoamide, and the 4-morpholinyl group is a morpholine bound to the methylene chair through the nitrogen atom of the morpholine ring.

The term "amino," as used herein, refers to —$NH_2$ or derivatives thereof formed by independent replacement of one or both hydrogen atoms thereon with a substituent or substituents independently selected from alkyl, alkanoyl, aryl, arylalkyl, cycloalkyl, cycloalkylalkyl, heteroaryl, heteroarylalkyl, and an amino protecting group. The term "$C_{1-10}$ alkoxy," as used herein, refers to a $C_{1-10}$ alkyl group, as defined herein, attached to the parent molecular group through an oxygen atom.

The term "$C_{1-10}$ alkyl" as used herein refers to a branched or unbranched hydrocarbon group of carbon atoms, such as methyl, ethyl, n-propyl, isopropyl, n-butyl, isobutyl, 1-butyl, and the like or branched or unbranched hydrocarbon groups of carbon atoms that either contain double or triple carbon bonds.

The term "$C_{1-10}$ alkylamino," as used herein, refers to a $C_{1-10}$ alkyl group, as defined herein, to which is attached at least one amino substituent. The term "$C_{3-15}$ cycloalkyl" as applied herein is meant to include cyclic hydrocarbon chains. Examples of these cyclic hydrocarbon chains include cyclopropane, cyclobutane, cyclopentane, cyclohexane, cycloheptane, cyclooctane, cyclononane, cyclodecane, cycloundecane, etc.

The term "$C_{2-12}$ dialkylamino," as used herein, refers to two $C_{1-10}$ alkyl groups, as defined herein, that are attached to an amino substituent. The term "$C_{1-10}$ fluoroalkyl," as used herein, refers to a $C_{1-10}$ alkyl group, as defined herein, to which is attached at least one fluorine substituent.

The term "$C_{1-10}$ perfluoroalkyl," as used herein, refers to a $C_{1-10}$ alkyl group in which all of the hydrogen atoms have been replaced with fluorine atoms. The term biotinyl, as use herein, refers to biotin without the biotin carboxyl hydroxyl group.

By the term "effective amount" of a compound as provided herein is meant a nontoxic but sufficient amount of the compound to provide the desired utility, for example to reduce, inhibit, prevent, or heal neuronal injury. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

The term "neurotoxin" means a compound that adversely affects cells of the nervous system. Suitable neurotoxins include compounds that induce axonal degeneration, for example by interfering with the neuronal cytoskeleton, in particular with microtubules. Microtubule stabilizers, for example Taxol® and Taccalonolides E and A, are preferred neurotoxins of the present invention. Taccalonolides E and A are described in Tinley T L et al. (2003) *Taccalonolides E and A. Plant-derived steroids with microtubule-stabilizing activity.* Cancer Res. June 15;63(12):3211-20, which is incorporated by reference in its entirety. Colchicine, colcemid, nocadazol, vinblastine and vincristine are additional exemplary neurotoxins that affect microtubules.

The term "Taxol®" is intended to be interchangeable with paclitaxel and refers to 5-beta,20-epoxy-1,2-alpha,4,7-beta,10-beta,13-alpha-hexahydroxy-tax-11-en-9-one 4,10-diacetate 2-benzoate 13-ester with (2R,3S)-N-benzoyl-3-phenyl-isoserine; 7,11-Methano-5H-cyclodeca[3,4]benz[1,2-b]oxete,benzenepropanoic acid derivative; Paclitaxel; TAX; Taxal; Taxol; Taxol A; substantially pure optical isomers, racemates, prodrugs, and derivatives thereof. The structure of paclitaxel is provided below.

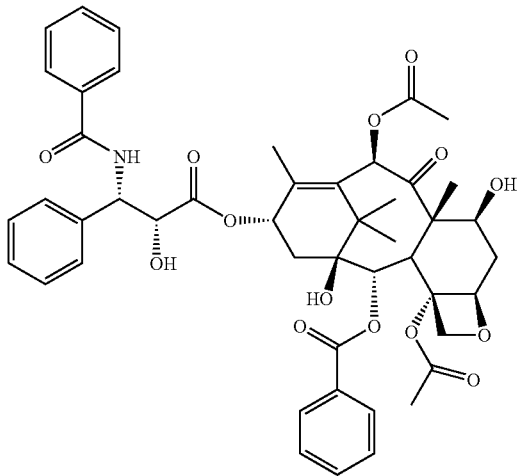

The term "anti-hyperproliferative agent" means a substance that reduces, inhibits or interferes with aberrant cell growth or division. Exemplary anti-hyperproliferative agents include but are not limited to anti-cancer agents such as paclitaxel, chemotherapy agents, anti-sense polynucleotides, enzymatic polynucleotides, polypeptides, dideoxy nucleotides, chain terminating nucleotides, antibodies, and small molecules.

The term "hyperproliferative disorder" means a pathology resulting from aberrant cell growth or division.

The term "calpain related pathology" means an abnormal cellular or systemic condition or symptom directly or indirectly caused, in part or in whole, by the activity of a calpain protease.

The term "pharmaceutically acceptable salt(s)", as used herein, unless otherwise indicated, includes salts of acidic or basic groups that may be present in the compounds of Formula I. The compounds of Formula I that are basic in nature are capable of forming a wide variety of salts with various inorganic and organic acids. The acids that may be used to prepare pharmaceutically acceptable acid addition salts of such basic compounds of Formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, TFA, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Those compounds of the Formula I that are acidic in nature, are capable of forming base salts with various pharmacologically acceptable cations. Examples of such salts include the alkali metal or alkaline earth metal salts and particularly, the sodium and potassium salts.

The term "pharmaceutically acceptable derivative" refers to any homolog, analog, or fragment corresponding to the peptide α-ketoamides of the present invention provided herein which inhibits protease activity and is relatively non-toxic to the subject or host.

The term "pharmaceutically acceptable" means a material that is not biologically or otherwise undesirable, i.e., the material may be administered to an individual along with the selected bicyclic compound without causing any undesirable biological effects or interacting in a deleterious manner with any of the other components of the pharmaceutical composition in which it is contained.

As used herein, and without limitation, the term "derivative" is used to refer to any compound which has a structure derived from the structure of the compounds of the present invention and whose structure is sufficiently similar to those disclosed herein and based upon that similarity, would be expected, by one skilled in the art, to exhibit the same or similar activities and utilities as the claimed compounds.

Exemplary Embodiments

Embodiments of the present invention describe compositions and methods for the treatment of a pathology, in particular a neural pathology such as cytoskeletal degeneration of peripheral neurons, peripheral neuropathy, or axonal degeneration including sensory neuron axonal degeneration. The neural pathology can be related to a disease or condition such as diabetes, or can be the result of contact with a chemcial agent including neurotoxic agents. One of the several embodiments of the present invention provides a method for treating a neural pathology of the peripheral nervous system, for example axonal degeneration, by administering to a patient a therapeutically effective amount of a compound of the formula I:

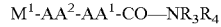

a pharmaceutically acceptable salt, or prodrug thereof, wherein $M^1$ is selected from the group consisting of H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—, Y—$SO_2$—, Y—O—CO—, Y—O—CS—, morpholine-CO—, and biotinyl;

X is selected from the group consisting of H, $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group, and $C_{1-10}$ alkyl monosubstituted with $M^2$;

Y is selected from the group consisting of $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group, $M^2$, and $C_{1-10}$ alkyl monosubstituted with $M^2$;

$M^2$ is selected from the group consisting of 2-furyl, 2-tetrahydrofuryl, 2-pyridyl, 3-pyridyl, 4-pyridyl, 2-pyrazinyl, 2-quinolinyl, 1-tetrahydroquinolinyl, 1-isoquinolinyl, 2-tetrahydroisoquinolinyl, and $—N(CH_2CH_2)_2O$;

J is selected from the group consisting of halogen, $CO_2H$, OH, CN, $NO_2$, $NH_2$, $C_{1-10}$ alkoxy, $C_{1-10}$ alkylamino, $C_{2-12}$ dialkylamino, $C_{1-10}$ alkyl-O—CO—, $C_{1-10}$ alkyl-O—CO—NH—, $C_{1-10}$ alkyl-S—, and $—N(CH_2CH_2)_2O$;

K is selected from the group consisting of halogen, $C_{1-10}$ alkyl, $C_{1-10}$ perfluoroalkyl, $C_{1-10}$ alkoxy, phenoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—, and $—N(CH_2CH_2)_2O$;

$AA^1$ and $AA^2$ side chain blocked or unblocked amino acids with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—$CO_2H$, alpha-aminoheptanoic acid, $NH_2$—CH($CH_2$-1-naphthyl)-$CO_2H$, $NH_2$—CH($CH_2$-2-naphthyl)-$CO_2H$, $NH_2$—CH($CH_2$-cyclohexyl)-$CO_2H$, $NH_2$—CH($CH_2$-cyclopentyl)-$CO_2H$, $NH_2$—CH($CH_2$-cyclobutyl)-$CO_2H$, $NH_2$—CH($CH_2$-cyclopropyl)-$CO_2H$, trifluoroleucine, 4-fluorophenylalanine, lysine substituted on the epsilon nitrogen with a biotinyl group, hexafluoroleucine, and $NH_2$—$CHR^2$—$CO_2H$;

$R^2$ is selected from the group consisting of $C_{1-10}$ branched and unbranched alkyl, $C_{1-10}$ branched and unbranched cyclized alkyl, and $C_{1-10}$ branched and unbranched fluoroalkyl;

$R^3$ and $R^4$ are selected independently from the group consisting of a) H, $C_{1-20}$ alkyl, $C_{1-20}$ cyclized alkyl, $C_{1-20}$ alkyl with a phenyl group attached to the $C_{1-20}$ alkyl, $C_{1-20}$ cyclized alkyl with an attached phenyl group, $C_{1-20}$ alkyl with an attached phenyl group monosubstituted with K, $C_{1-20}$ alkyl with an attached phenyl group disubstituted with K, $C_{1-20}$ alkyl with an attached phenyl group trisubstituted with K, $C_{1-20}$ cyclized alkyl with an attached phenyl group monosubstituted with K, $C_{1-10}$ alkyl with a morpholine [—N($CH_2CH_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), —NH—$CH_2CH_2$-(3-indolyl);

b) —$CH_2CH(OH)$—$R^5$, and c) —$(CH_2)_n$—$R^7$;

$R^5$ is selected from the group consisting of phenyl, phenyl monosubstituted with J, phenyl disubstituted with J, phenyl trisubstituted with J, pentafluorophenyl,

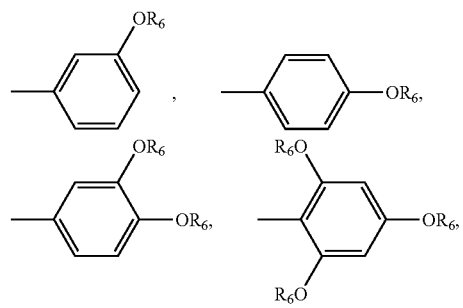

1-naphthyl, 1-naphthyl monosubstituted with J, 1-naphthyl disubstituted with J, 2-naphthyl, 2-naphthyl monosubstituted with J, 2-naphthyl disubstituted with J, 2-pyridyl, 2-quinolinyl, and 1-isoquinolinyl;

$R^6$ is selected from the group consisting of $C_{1-4}$ alkyl, $C_{1-4}$ alkyl substituted with phenyl, phenyl, and phenyl substituted with J;

n=1-6;

$R^7$ is selected from the group consisting of 2-furyl, 2-furyl monosubstituted with J, 2-pyridyl, 2-pyridyl monosubstituted with J, 3-pyridyl, 3-pyridyl monosubstituted with J, 4-pyridyl, 4-pyridyl monosubstituted with J, 2-quinolinyl, 2-quinolinyl monosubstituted with J, 1-isoquinolinyl, 1-isoquinolinyl monosubstituted with J,

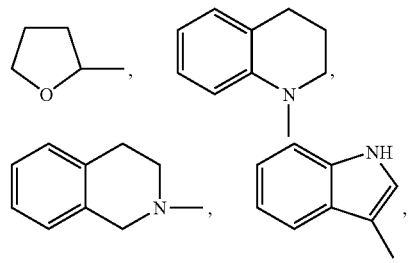

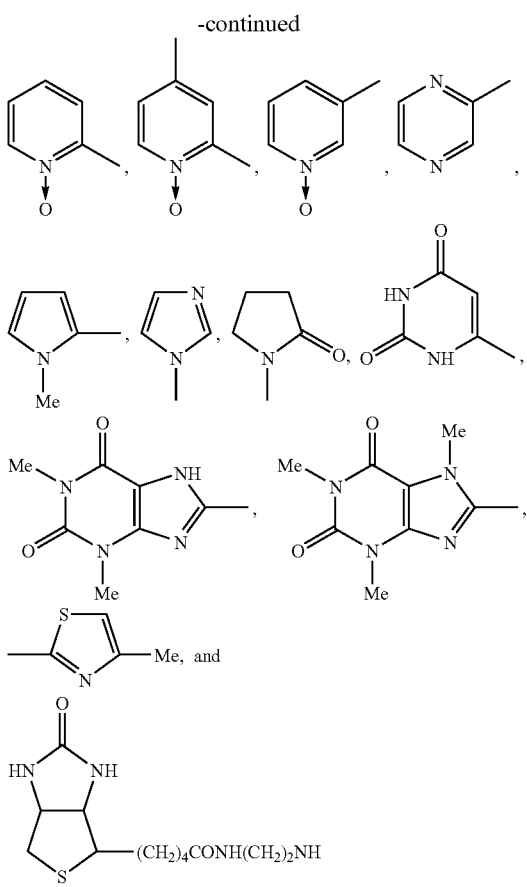

Aspects of the present invention provide compositions and methods for treating neural pathologies by targeting axonal degeneration rather than by preventing the death of whole neurons or stimulating the growth of whole neurons. By inhibiting or preventing axonal degeneration, embodiments of the invention can maintain axonal connections between neurons and between neurons and their targets thereby preventing or reducing neuropathy. Axonal degeneration can occur over extended periods of time and, therefore, other embodiments of the invention are directed to compositions and methods for treating chronic pathologies resulting in axonal degeneration rather than rapid onset pathologies such as stroke.

The compounds of the present invention can be administered in an amount sufficient to inhibit, reduce, or ameliorate a pathology of the peripheral nervous system including but not limited to peripheral neuropathy, sensory neuron axonal degeneration, cytoskeletal degeneration of neurons of the peripheral nervous system, toxin-induced peripheral nerve cell damage, and calpain-related neuronal pathology. It will be appreciated by one of skill in the art that some embodiments of the present invention are directed to compositions and methods of treating pathologies of peripheral nervous system and not of the central nervous system.

Other embodiments of the invention describe compositions and methods of treating chronic degeneration of motor and or sensory neurons as may be seen in motor neuron diseases, peripheral neuropathies due to chronic systemic diseases (i.e., diabetes, uremia, liver diseases, infections, rheumatologic disorders), genetic mutations (hereditary motor/sensory and hereditary sensory neuropathy groups, including all Charcot-Marie-Tooth disorders), demyelinating neuropathies with secondary axonal degeneration (Guillain-Barre group) and idiopathic neuropathies, demyelinating disorders of the central nervous system including multiple sclerosis, and chronic spinal cord degenerations, genetically based and otherwise, comprising the step of administering to a patient a therapeutically effective amount of a compound of formula I.

Yet another embodiment of the invention provides a pharmaceutical composition including an anti-hyperproliferative agent in combination with a calpain inhibitor, for example a peptide α-ketoamide. Exemplary anti-hyperproliferative agents include microtubule stabilizing agents such as paclitaxel also referred to as Taxol®. Suitable peptide α-ketoamides include those of formula I. These compositions provide an anti-hyperproliferative effective amount of a anti-cancer agent with an effective amount of an agent for reducing the side effects associated with the anti-cancer agent. Thus, embodiments of the present invention disclose compositions comprising a combination of anti-cancer agents, for example paclitaxel, and peptide α-ketoamide calpain inhibitors. One of skill in the art will appreciate that the peptide α-ketoamide calpain inhibitors of the present invention do not directly treat hyperproliferative disorders, but instead, are used in combination with anti-cancer agents to minimize side effects of anti-cancer agents.

Still another embodiment of the present invention provides a method of treating a hyperproliferative disorder by administering a pharmaceutical composition comprising a anti-hyperproliferative agent in combination with a calpain inhibitor. Anti-hyperproliferative agents include microtubule stabilizers such as paclitaxel, and suitable calpain inhibitors include peptide α-ketomides, for example AK295. AK295 is a potent transition-state reversible inhibitor for both calpain I ($K_I$=0.14 μM) and calpain II ($K_I$=0.041 μM), and is a less effective inhibitor of other cysteine proteases such as cathepsin B [Li, Z., A.-C. Ortega-Vilain, G. S. Patil, D.-L. Chu, J. E. Foreman, D. D. Eveleth and J. C. Powers (1996). "Novel peptidyl α-keto amide inhibitors of calpains and other cysteine proteases." *J. Med. Chem.* 39(20): 4089-4098.]. The calpain inhibitor can be administered concurrently with the anti-proliferative agent or subsequent to the administration of the anti-proliferative agent. Additionally, the calpain inhibitor can inhibit one or both of calpain I and calpain II.

Representative peptide α-ketoamides of the invention include but are not limited to:
Z-Leu-Nva-CO—NH—$CH_2$-2-pyridyl,
Z-Leu-Abu-CO—NH—$CH_2CH(OH)C_6F_5$,
Z-Leu-Phe-CO—NH—$(CH_2)_2$Ph,
Z-Leu-Abu-CO—NH—$CH_2CH(OH)C_6H_4$-3-$OC_6H_4$(3-$CF_3$),
Z-Leu-Abu-CO—NH—$CH_2CH(OH)C_6H_4$(4-$OCH_2$Ph),
Z-Leu-Abu-CO—NH—$CH_2CH(OH)C_6H_4$(4-OPh),
Z-Leu-Phe-CO—NH—$CH_2$-2-quinolinyl,
Z-Leu-Abu-CO—NH—$(CH_2)_2C_6H_4$(3-$OCH_3$),
Z-Leu-Abu-CO—NH—$(CH_2)_2C_6H_4$(4-$OCH_3$),
Z-Leu-Abu-CO—NH—$CH_2CH(OH)$-1-$C_{10}H_7$,
Z-Leu-Phe-CO—NH—$(CH_2)_3$-4-morpholinyl,
Z-Leu-Abu-CO—NH—$(CH_2)_2C_6H_4$(2-$OCH_3$),
Z-Leu-Abu-CO—NH—$CH_2$-2-quinolinyl,
Z-Leu-Abu-CO—NH—$(CH_2)_3$-4-morpholinyl (AK295),
Z-Leu-Abu-CO—NH—$(CH_2)_2$-2-(N-methylpyrrole),
Z-Leu-Phe-CO—NH—$CH_2CH(OH)C_6H_4$-3-$OC_6H_4$(3-$CF_3$),
Z-Leu-Abu-CO—NH—$(CH_2)_2C_6H_5$,
Z-Leu-Phe-CO—NH-Et,
Z-Leu-Abu-CO—NH—$CH_2CH(OC_2H_5)_2$, Z-Leu-Phe-CO—NH—CH$_2$CH(OH)C$_6$H$_4$(4-OPh),
Z-Leu-Phe-CO—NH—CH$_2$CH(OH)C$_6$H$_4$(4-OCH$_2$Ph),
Z-Leu-Abu-CO—NH—CH$_2$C$_6$H$_5$,
Z-Leu-Phe-CO—NH—(CH$_2$)$_2$NH-biotinyl,
Z-Leu-Phe-CO—NH—(CH$_2$)$_3$-2-tetrahydroisoquinolinyl,
Z-Leu-Abu-CO—NH—CH$_2$CH(OH)C$_6$H$_3$(3,4-(OCH$_2$Ph)$_2$),
Z-Leu-Abu-CO—NH—CH$_2$CH(OH)C$_6$H$_4$(4-OCH$_3$),
Z-Leu-Nva-CO—NH—(CH$_2$)$_3$-4-morpholinyl,
Z-Leu-Abu-CO—NH—CH$_2$-1-isoquinolinyl,
Z-Leu-Abu-CO—NH-Et,
Z-Leu-Abu-CO—NH—CH$_2$CH(OH)C$_6$H$_4$-3-OC$_6$H$_3$(3,4-Cl$_2$),
Z-Leu-Abu-CO—NH-Me,
Z-Leu-Abu-CO—NH—(CH$_2$)$_3$-1-imidazolyl,
Z-Leu-Abu-CO—NH—(CH$_2$)$_2$-3-indolyl,
Z-Leu-Abu-CO—NH—(CH$_2$)$_3$-2-tetrahydroisoquinolinyl,
Z-Leu-Abu-CO—NH—CH$_2$-2-tetrahydrofuryl,
Z-Leu-Abu-CO—NH—CH$_2$CH(OH)C$_6$H$_4$(4-N(CH$_3$)$_2$),
Z-Leu-Phe-CO—NH-n-Pr,
Z-Leu-Abu-CO—NH—CH$_2$CH(OH)-2-C$_{10}$H$_7$,
Z-Leu-Phe-CO—NH-Me,
Z-Leu-Abu-CO—NH—CH$_2$CH(OH)C$_6$H$_4$(3-CF$_3$),
Z-Leu-Abu-CO—NH—(CH$_2$)$_3$-1-tetrahydroquinolinyl,
Z-Leu-Abu-CO—NH—(CH$_2$)$_2$C$_6$H$_4$(4-OH),
Z-Leu-Abu-CO—NH—CH$_2$CH(OH)C$_6$H$_2$(3,4,5-(OCH$_3$)$_3$),
Z-Leu-Phe-CO—NH—(CH$_2$)$_3$-1-tetrahydroquinolinyl,
Z-Leu-Abu-CO—NH—(CH$_2$)$_2$-2-pyridyl,
Z-Leu-Abu-CO—NH—CH$_2$-C$_6$H$_7$(1,3,3-(CH$_3$)$_3$-5-OH),
Z-Leu-Phe-CO—NH—CH$_2$CH(OH)C$_6$H$_4$(3-CF$_3$),
Z-Leu-Phe-CO—NH—CH$_2$CH(OH)C$_6$H$_3$(3,4-(OCH$_2$Ph)$_2$),
Z-Leu-Abu-CO—NH—(CH$_2$)$_5$OH,
Z-Leu-Abu-CO—NH—CH$_2$CH(OCH$_3$)$_2$,
Z-Leu-Phe-CO—NH—CH$_2$CH(OH)C$_6$H$_4$-3-OC$_6$H$_3$(3,4-Cl$_2$),
Z-Leu-Phe-CO—NH—CH$_2$CH(OH)C$_6$H$_4$(3-OPh),
Z-Leu-Phe-CO—NH—CH$_2$CH(OH)C$_6$H$_4$(4-N(CH$_3$)$_2$),
Z-Leu-Abu-CO—NH—CH$_2$-2-pyridyl,
Z-Leu-Abu-CO—NH—(CH$_2$)$_2$O(CH$_2$)$_2$OH,
Z-Leu-Phe-CO—NH—CH$_2$-2-pyridyl,
Z-Leu-Abu-CO—NH—(CH$_2$)$_2$NH-biotinyl,
Z-Leu-Abu-CO—NH—CH$_2$—C$_6$H$_{11}$,
Z-Leu-Phe-CO—NH—CH$_2$CH(OH)C$_6$F$_5$,
Z-Leu-Abu-CO—NH—CH$_2$-2-furyl,
Z-Leu-Abu-CO—NH—(CH$_2$)$_3$C$_6$H$_5$,
Z-Leu-Abu-CO—NH—(CH$_2$)$_2$OH,
Z-Leu-Abu-CO—NH—CH$_2$CH(OH)C$_6$H$_4$(3-OPh),
Z-Leu-Abu-CO—NH—(CH$_2$)$_2$-4-morpholinyl,
Z-Leu-Abu-CO—NH—CH$_2$CH(OH)Ph,
Z-Leu-Abu-CO—NH—CH$_2$-4-pyridyl,
Z-Leu-Abu-CO—NH—(CH$_2$)$_3$-1-pyrrolidine-2-one,
Z-Leu-Phe-CO—NH—CH$_2$CH(OH)Ph,
Z-Leu-Abu-CO—NH—CH$_2$C$_6$H$_3$(3,5-(OCH$_3$)$_2$),
Z-Leu-Nva-CO—NH—CH$_2$CH(OH)Ph,
Z-Leu-Abu-CO—NH—CH$_2$-8-caffeinyl,
Z-Leu-Abu-CO—NH-n-Pr,
Z-Leu-Abu-CO—NH—CH$_2$-3-pyridyl, and
Z-Leu-Phe-CO—NH—CH$_2$Ph.

Microtubule destabilizing agents, for example paclitaxel are a highly effective anti-cancer agents that cause peripheral neuropathy as its major toxic side effect. Thus, the present invention includes compositions and methods for treating hyperproliferative disorders such as cancer with an anti-cancer agent in combination with a calpain inhibitor for treating the side effects of the anti-cancer agent. Neuropathy is characterized by degeneration of sensory axons, which may be severe enough to be dose limiting. It has been discovered that peptide α-ketoamide calpain inhibitors, for example AK295, are effective in reducing the clinical and pathological effects of neurotoxins such as paclitaxel. The combination of anti-hyperproliferative agents with peptide α-ketoamides provides a therapeutic agent that is effective in treating hyperproliferative disorders such as cancer, while minimizing the side-effects of the anti-proliferative agent. It has been discovered that AK295 reduced the severity of axonal degeneration caused by paclitaxel in dorsal root ganglion cultures. In mice, AK295 similarly reduced the degree of axonal degeneration in sensory nerve roots, and improved clinical measures of neuropathy, including behavioral and electrophysiological function. Peptide α-ketoamides given systemically inhibit calpains and can improve neurologic function in a clinically relevant model of toxic neuropathy. Without being bound by theory, it is believed that peptide α-ketoamides work to prevent neuropathy by inhibiting axonal degeneration. Peptide α-ketoamides can thus be used in other neurological disorders where axonal degeneration is a major feature.

Chronic calpain inhibition with compositions disclosed herein, prodrugs, or pharmaceutically acceptable derivatives thereof, are effective in treating chronic axonal degeneration after exposure to a neurotoxic agent. No toxic side effects of AK295 either in culture or in the animal were identified, further encouraging the potential usefulness of this agent for long-term treatments.

The mechanism of paclitaxel neuropathy is poorly understood. Microtubule aggregation in neurons, axons, and Schwann cells has been suggested as a possible mechanism. The data provided herein demonstrate that paclitaxel aggregates microtubules and kills cells in culture even in the presence of AK295. The data also show that paclitaxel can directly activate calpains, and that this activation is prevented by AK295. Without being bound by any one theory, calpain activation may result from a variety of pathological processes, and represents a "final common pathway" leading to cytoskeletal breakdown and axonal degeneration. Thus, calpain inhibition may be protective in many disorders where axonal degeneration is a prominent feature. Other diseases likely to positively effected by peptide α-ketoamide calpain inhibitors are peripheral neuropathies due to genetic mutations, peripheral neuropathies associated with other systemic diseases including uremia, rheumatologic diseases, liver diseases, and infections, axonal degeneration secondary to primary demyelinating disorders including inflammatory demyelinating neuropathies and multiple sclerosis [Waxman, S. G. (1998). "Demyelinating diseases—new pathological insights, new therapeutic targets [editorial; comment]." *N Engl J Med* 338(5): 323-5].

Administration

This invention also provides a pharmaceutical composition which comprises a compound according to Formula I and a pharmaceutically accepted carrier, diluent or excipient, optionally in combination with an anti-hyperproliferative agent. Accordingly, the compounds of Formula I may be used in the manufacture of a medicament. For therapeutic use, the peptide α-ketoamides may be administered orally, topically, or parenterally. The term parenteral, as used, includes subcutaneous injection, intravenous, intramuscular, intrasternal injection, or infusion techniques. The dosage depends primarily on the specific formulation and on the object of the therapy or prophylaxis. The amount of the individual doses as well as the administration is best determined by individually assessing each case.

The pharmaceutical compositions containing the active ingredient may be in a form suitable for oral use, for example, as tablets, troches, lozenges, aqueous or oily suspensions, dispersible powders or granules, emulsions, hard or soft capsules, syrups, or elixirs. Dosage levels of the order of 0.2 mg to 140 mg per kilogram of body weight per day are useful in the treatment of the above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the peptideα-ketoamides or their pharmaceutically acceptable salts, derivatives or prodrugs will normally be in the dosage range from 0.2 to 140 mg/kg of body weight. Administration is made by intravenous, intramuscular, or subcutaneous injection. Accordingly, pharmaceutical compositions for parenteral administration will contain from about 10 mg to 7 gms of the compounds per dose. In addition to the active ingredient, these pharmaceutical compositions will usually contain a buffer, e.g. a phosphate buffer which keeps the pH in the range from 3.5 to 7 and sodium chloride, mannitol, or sorbitol for adjusting the isotonic pressure.

A composition for topical application can be formulated as an aqueous solution, lotion, jelly or an oily solution or suspension. A composition in the form of an aqueous solution is obtained by dissolving the compounds of this invention in aqueous buffer solution of pH 4 to 6.5 and, if desired, adding a polymeric binder. An oily formulation for topical application is obtained by suspending the compounds of this invention in an oil, optionally with the addition of a swelling agent such as aluminium stearate and/or a surfactant.

Materials and Methods

Paclitaxel-induced Axonal Degeneration in Rat DRG Culture

Dorsal Root Ganglion (DRG) from E15 rats were dissected and stripped from connective tissue into L15 medium (GIBCO), washed twice with PBS, and plated in collagen coated dishes containing DMEM with 1% N2 supplement and 7S NGF (100 ng/ml). Cultures were kept at 37° C., 5% $CO_2$. After 5 days of growth, media was changed to that containing test agents (paclitaxel, AK 295), and DRG remained in culture for an additional 10 days. Paclitaxel was dissolved in Cremophor EL/ethanol (50:50); final concentration of Cremophor EL and ethanol in cultures are less than 0.0001%. AK295 was dissolved in DMSO with a final concentration of DMSO in culture of 0.05%. This amount of DMSO demonstrated no effects on DRG growth.

Serial Images of DRG were captured on day 0, 4, 8 and 10. The area of the DRG halo at each time point was normalized to the area measured on day 0 (day test agents added), enabling each DRG to serve as its own control. Data were subjected to ANOVA, with post-test correction for multiple comparisons.

Paclitaxel Neuropathy and AK295 Treatment in Mice

Eight-week-old female C57BL/6J mice were separated into 4 treatment groups as outlined in FIG. 1. All groups were treated with paclitaxel and two groups were treated with a combination of paclitaxel and AK295. Three-week and 6-week protocols were investigated. paclitaxel was dissolved 50/50 in Cremophor EL/ethanol and diluted 1:1 with saline; final concentration was 7.5 mg/ml. Each paclitaxel treatment consisted of 3 injections of 60 mg/kg into the jugular vein on an every other day schedule. The 3-week groups received one paclitaxel treatment and the 6-week groups received two paclitaxel treatments. Control groups were treated with the Cremaphor diluent only.

AK295 (Z-Leu-Abu-(CH$_2$)$_3$-4-morpholinyl) was synthesized as previously described [Li, Z., A.-C. Ortega-Vilain, G. S. Patil, D.-L. Chu, J. E. Foreman, D. D. Eveleth and J. C. Powers (1996). "Novel peptidyl a-keto amide inhibitors of calpains and other cysteine proteases." J. Med. Chem. 39(20): 4089-4098]. The AK295 treatment groups received subcutaneous injections of AK295 (48 mg/kg) with each paclitaxel injection. After the last paclitaxel injection, a 100 µl Alzet pump (Alza Corporation, Mountain View, Calif.) filled with AK295 (84 mg/ml in DMSO/PEG 300, 1:1), was surgically implanted under the back skin. These pumps are designed to deliver drug at a rate of 6 µl per day for 14 days, translating into 0.504 mg/day, or 24 mg/kg/day for an average 18 g mouse. The 6-week treatment group received AK295 injections with the second paclitaxel treatment and had a new pump implanted for the remainder of the study. Control animals received initial injections with diluent only, and received pumps containing diluent only.

Animals were killed by perfusion with 4% paraformaldehyde (in 0.1M PBS buffer, pH 7.4) at the time points depicted in FIG. 1. The nerve roots (L4 dorsal and ventral) were harvested and post fixed overnight in 5% buffered glutaraldehyde at 4° C. Nerve roots were rinsed with PBS buffer, processed by standard methods, and embedded in plastic for light microscopy. Sections of 780 nm were stained with toluidine blue for microscopy study and image analysis.

Image Analysis

Images of dorsal and ventral roots (125×) were captured using a Kodak DCS-5 digital camera attached to an Olympus BH-2 microscope. Multiple overlapping images were captured, including all axons within the cross section. These images were combined into a montage so that the individual nerve fibers did not appear more than once. Images were analyzed using ImagePro software (Media Cybernetics, Silver Spring, Md.) running on a Gateway personal computer. All myelinated axons were counted. Axonal density was calculated by dividing the number of axons by the area of nerve cross-section. The diameter and area of each remaining axon was measured by tracing the inner boarder of myelin. All data were subjected to ANOVA.

Behavioral Testing

To evaluate changes in neuromuscular function, animals were subjected to testing on a Rotarod apparatus (Columbus Instruments, Columbus, Ohio) before paclitaxel treatments and prior to sacrifice. The initial speed was set at 1.6 rpm with acceleration rate of 4 rpm/min. Animals were acclimated to the Rotarod for three consecutive days before the test date. The test was repeated 3 times during each testing session with at least 2 minutes of rest between each test. The best performance of each session was recorded. Percent changes were calculated and analyzed using ANOVA with post-test comparisons.

Electrophysiology

Nerve conduction studies were performed using standard equipment (Nicolet, Madison, Wis.) on anesthetized animals on the same schedule as Rotarod testing. For hind limb recording, the recording electrodes were inserted into the interosseous muscles of the left foot; stimuli were administered at the ankle and at the hip (sciatic notch) close to the tibial and sciatic nerve, respectively. A ground electrode was inserted subcutaneously into the tail. Compound muscle action potentials were recorded (maximum) and nerve conduction velocities were calculated. For tail nerve recording, the recording electrodes were placed at the base of the tail, keeping the anode and the cathode approximately 5 mm apart. Stimuli were administered 4-5 cm distal. A ground electrode was placed in between the stimulus and recording electrodes. The sensory nerve action potential was averaged over 50-80 stimuli, and the amplitude was recorded. Sensory conduction velocity was also calculated.

Calpain Activation Assay:

PC12 cells were grown for 24 hours in DMEM with 10% horse and 5% fetal calf serums. Calpain activity in response to paclitaxel was assessed in relation to dose (1, 10, 50, or 100 ng/ml for 24 hours) and of time of exposure (10 ng/ml of paclitaxel for up to 48 hours). After exposure, cells were suspended in KRH buffer (25 mM Na-HEPES, 115 mM NaCl, 5 mM KCl, 1 mM KH2PO4, 1.2 mM MgSO4, 2 mM CaCl2, 0.2%1 BSA, pH 7.4) and 2 ml of cell suspension was transferred to test tube. The reaction was started by adding 100 μL of the cell-permeable calpain substrate (Suc-Leu-Leu-Val-Tyr-AMC, 0.84 mg/ml). The suspension was mixed immediately and incubated at 37° C. for 15 minutes. The reaction was stopped by adding 100 μL 0.4 N HCl. After sonication and centrifugation, free AMC in the supernatant was measured using a microplate reader ($\lambda_{ex}355/\lambda_{em}460$). A standard curve was constructed using AMC standard. Calpain activity was expressed as AMC concentration (pM) per $10^6$ cells.

Imaging of Microtubule Aggregates:

PC12 cells were cultured on collagen-coated coverslips for 48 hours and then treated for 24 hours with paclitaxel or AK 295. After treatment cells were fixed with 4% paraformaldehyde for 30 minutes and post-fixed with pre-cooled methanol for 5 minutes at −20° C. The cells was then rinsed with PBS and stained with antibody to α-tubulin using standard immunofluorescence staining methods. The cells were imaged on a Zeiss LSM 510 confocal microscope for identification of microtubule aggregates and mitotic figures.

Cytotoxicity Assay:

PC12 cells were cultured in 96 well plates containing DMEM supplemented with 10% horse serum and 5% fetal calf serum, 200 μl/well. At 80% confluence 100 μl medium was replaced with 50 μl Sytox® (Molecular Probes, www.molecularprobes.com, final concentration 4 μM) and 50 μl of the experimental compounds (paclitaxel 10, 100, 200 or 100 ng/ml, AK295, 50 μM). The caspase inhibitor JG36 (Cbz-Asp-Glu-Val-AAsp-EP-COOEt) was synthesized in our laboratory. JG36 is highly active against caspase-3 and little activity against other cysteine proteases [Asgian, J. L., K. E. James, Z. Z. Li, W. Carter, A. J. Barrett, J. Mikolajczyk, G. S. Salvesen and J. C. Powers (2002). "Aza-peptide epoxides: a new class of inhibitors selective for clan CD cysteine proteases." *J Med Chem* 45(23): 4958-60.]. Fluorescence ($\lambda_{ex}485/\lambda_{em}538$) was measured immediately and at scheduled time points for up to 24 hours. After the last reading, 50 μl of 4% paraformaldehyde was added to each well and the plate was kept at 4° C. for one hour followed by a final reading for the maximal amount of fluorescence release. The experimental protocol was repeated three times.

EXAMPLES

Example 1

AK295 Protects Against Paclitaxel-induced Axon Degeneration in DRG Culture

Figure 2:
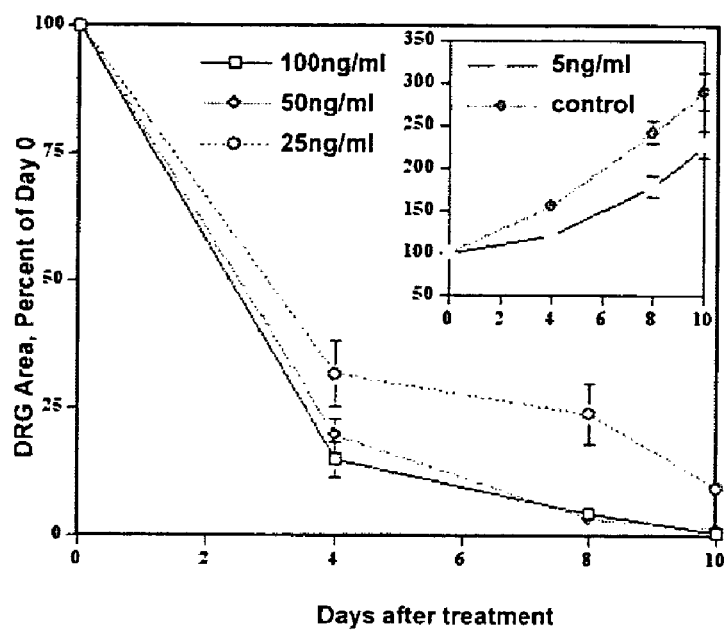
FIG. 2 is a line graph showing dose-dependent axonal degeneration in DRG cultures. Note that control cultures continue to grow (inset) while those exposed to paclitaxel demonstrate either slowed growth (5 ng/ml, inset) or progressive axonal death.
Figure 3:
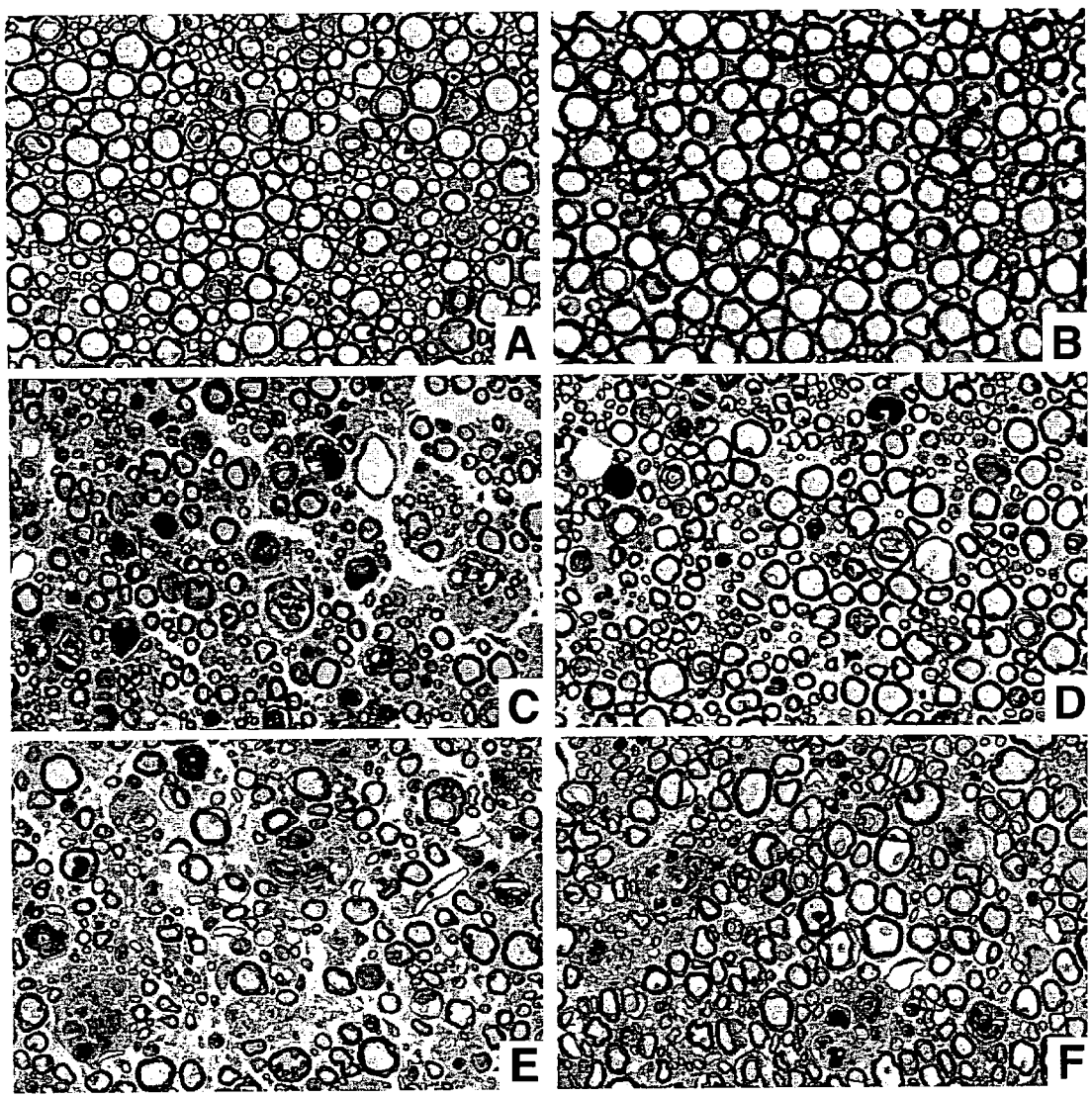
FIGS. 3A-F are photomicrographs of nerve fiber pathology. A) control dorsal root; B) ventral root from paclitaxel-treated mouse; C) dorsal root, paclitaxel, 3 weeks; D) dorsal root, paclitaxel and AK295, 3 weeks. E) dorsal root, paclitaxel, 6 weeks; F) dorsal root, paclitaxel and AK295, 6 weeks. Note that the ventral root is unaffected and that the AK295-treated animals show significantly fewer degenerating fibers. All photomicrographs×60.

Exposure to paclitaxel caused dose-dependent axonal degeneration in cultured dorsal root ganglia. Doses of 25 ng/ml or greater caused rapid axonal degeneration; a dose of 5 ng/ml did not cause obvious degeneration but did slow axonal growth (FIG. 2). Degeneration occurred in a distal to proximal pattern ("dying back") similar to that seen in DRG cultures exposed to vincristine [Wang, M. S., Y. Wu, D. G. Culver and J. D. Glass (2000). "Pathogenesis of axonal degeneration: parallels between Wallerian degeneration and vincristine neuropathy." *Journal of Neuropathology and Experimental Neurology* 59(7): 599-606.]. Addition of AK295 (50 μM) to the culture media provided about 50% protection against axonal degeneration induced by 25 ng/ml paclitaxel for up to 8 days, as measured by the area of the DRG halo (data not shown).

Example 2

AK295 Protects Against Paclitaxel Neuropathy in Mice

Paclitaxel caused dose-dependent axonal degeneration in mice. Two doses (3×30 mg/kg and 3×60 mg/kg) were tested. The low dose caused axonal degeneration in relatively few fibers, with inconsistent numbers of degenerating fibers (data not shown). The higher dose caused degeneration of a significant number of sensory fibers (FIGS. 3A-F), which was reproducible and suitable for our purpose of quantitative analysis. paclitaxel did not cause axonal degeneration in motor fibers.

Figure 4:
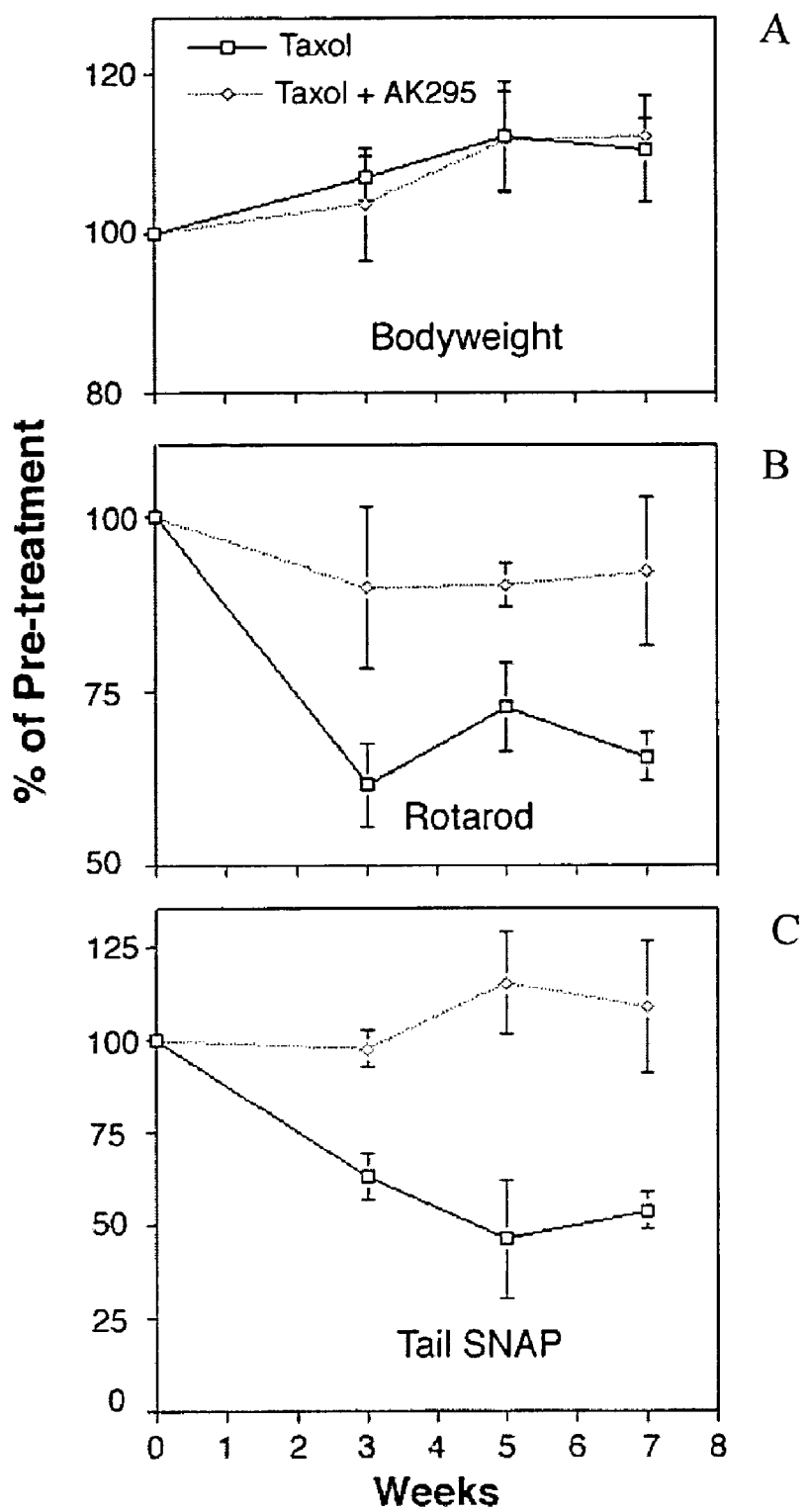
FIGS. 4A-C are line graphs showing clinical characteristics of animals treated with paclitaxel, paclitaxel+AK295, and controls. Data are plotted as % change as compared to pre-treatment values. SNAP=tail sensory nerve action potential amplitude. (*p<0.05).
Figure 5:
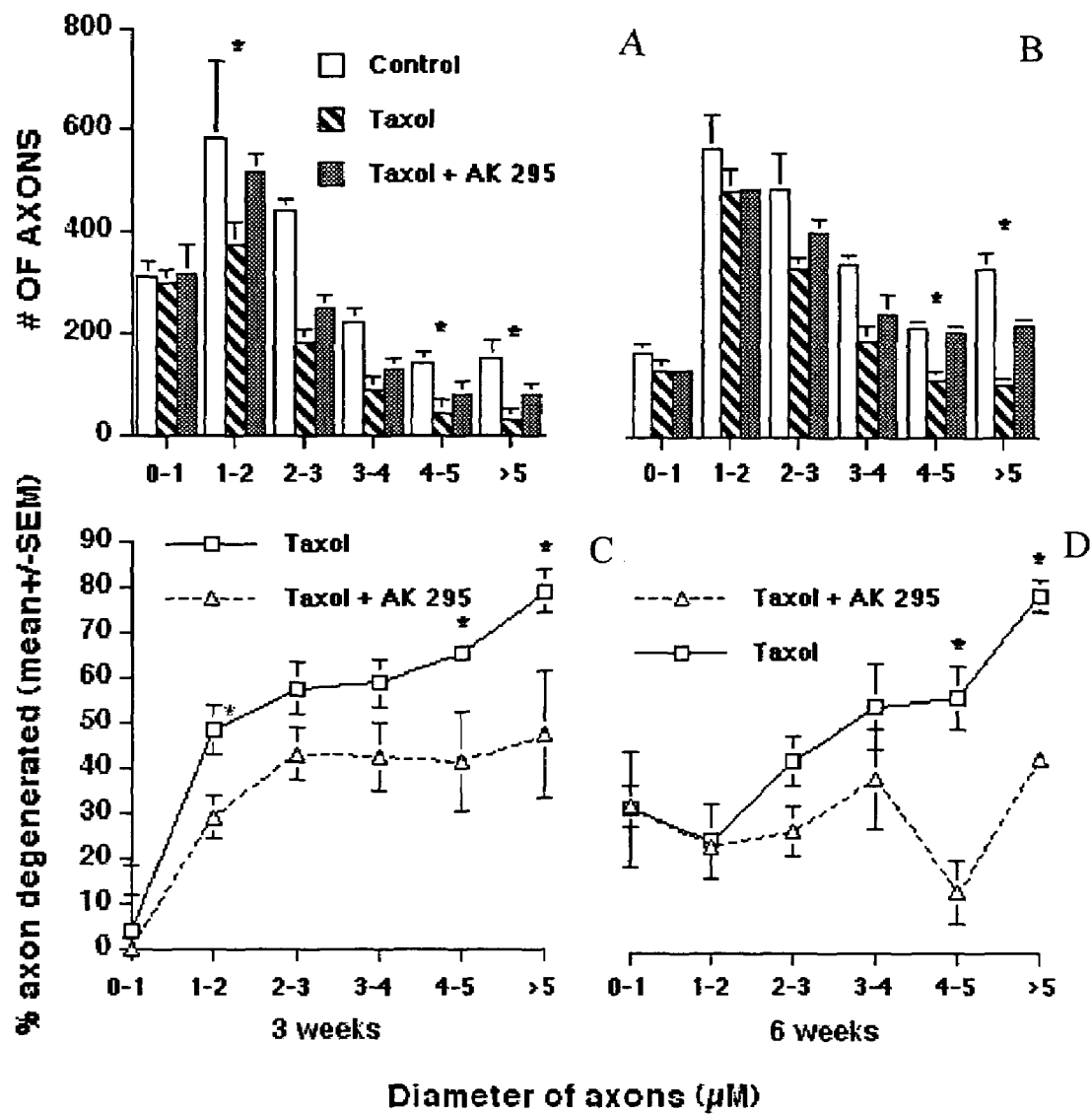
FIGS. 5A-D are graphs showing quantitative data of dorsal roots. Panels A and B show the distribution of remaining nerve fibers by fiber diameter, and panels C and D show the percentage of fibers lost in each size group. Note that the number of small fibers decreases with age, reflecting axonal growth.

Nineteen mice were used for the 3-week protocol: control (4), paclitaxel (7) and paclitaxel plus AK295 (8). Ten mice were used for the 6-week protocol: control (4), paclitaxel (3) and paclitaxel plus AK 295 (3). The animals treated with paclitaxel or paclitaxel plus AK295 showed weight loss of 1 to 3 grams in the first week, but regained a normal growth rate and were in good health for the remainder of the study (FIGS. 4A-C). Rotarod and electrophysiological measures supported the presence of peripheral neuropathy (FIG. 4), and pathological analysis of dorsal roots demonstrated significant loss of myelinated fibers at the 3-week time point (Table 1). There was little evidence of further progression of neuropathy in animals receiving a second paclitaxel treatment during the fourth week and evaluated at the 6-week time point. Pilot experiments, however, demonstrated almost full recovery of myelinated fiber numbers at 6 weeks in animals not receiving a second paclitaxel treatment (data not shown), suggesting that the second paclitaxel treatment had the effect of maintaining the neuropathy in animals that otherwise would have recovered. Analysis of fibers grouped by diameter demonstrated that axonal loss was most prominent in larger fibers (FIGS. 5A-D), as has been demonstrated in paclitaxel neuropathy in humans and rats.

AK295 treatment was protective against paclitaxel induced neuropathy by all measures. Behavioral and electrophysiological testing showed protection in the AK295 group at 3 weeks that persisted to 6-week time point (FIGS. 4A-D). Comparing pre- and post-treatment measures, animals treated with diluent only improved by about 20% on the Rotarod (not shown), whereas performance in Paclitaxel-treated mice was reduced to about 60% of baseline. Paclitaxel+AK295-treated mice remained at baseline levels. Similar results were obtained from sensory nerve conduction studies. Tail SNAP in Paclitaxel-treated mice was reduced to about 50% of baseline, whereas paclitaxel+AK295-treated mice showed no reduction in sensory amplitudes. There were no significant effects of paclitaxel on motor conduction studies in either sciatic or tail nerves (not shown).

Pathologically, the degree of axonal degeneration was less in AK295-treated mice as compared to mice treated with paclitaxel only (FIGS. 3A-F and Table 1). Quantitative analysis demonstrated an increase in fiber number and density at both 3 and 6 weeks in the AK295 group (Table 1). Mean fiber diameter was also increased toward normal in these groups (Table 1). Subgroup analysis of the effects of paclitaxel and AK295 by fiber size demonstrated the large-fiber predominance of paclitaxel toxicity and the relative protection by AK295 in these larger fibers (FIGS. 5A-D).

TABLE 1

Morphometry of dorsal root axons, mean ± SEM

| Groups | Total Axons | Mean Axon Diameter | Axons/mm² |
|---|---|---|---|
| Control, 3 w | 2168 ± 173 | 2.37 ± 0.11 | 33760 ± 1731 |
| Paclitaxel, 3 w | 1099 ± 76 | 1.89 ± 0.08 | 26806 ± 2496 |
| paclitaxel + AK295, 3 w | 1378 ± 96* | 2.08 ± 0.13 | 29134 ± 1569 |
| Control, 6 w | 2107 ± 141 | 3.09 ± 0.13 | 28207 ± 2175 |
| Paclitaxel, 6 w | 1350 ± 98 | 2.56 ± 0.12 | 17733 ± 1654 |
| paclitaxel + AK295, 6 w | 1620 ± 73* | 3.10 ± 0.04* | 19560 ± 1061 |

*$p < 0.05$, paclitaxel + AK295 vs. paclitaxel only. 3 w = 3 weeks, 6 w = 6 weeks.

Example 3

Paclitaxel-induced Calpain Activation in PC12 Cells

Figure 6:
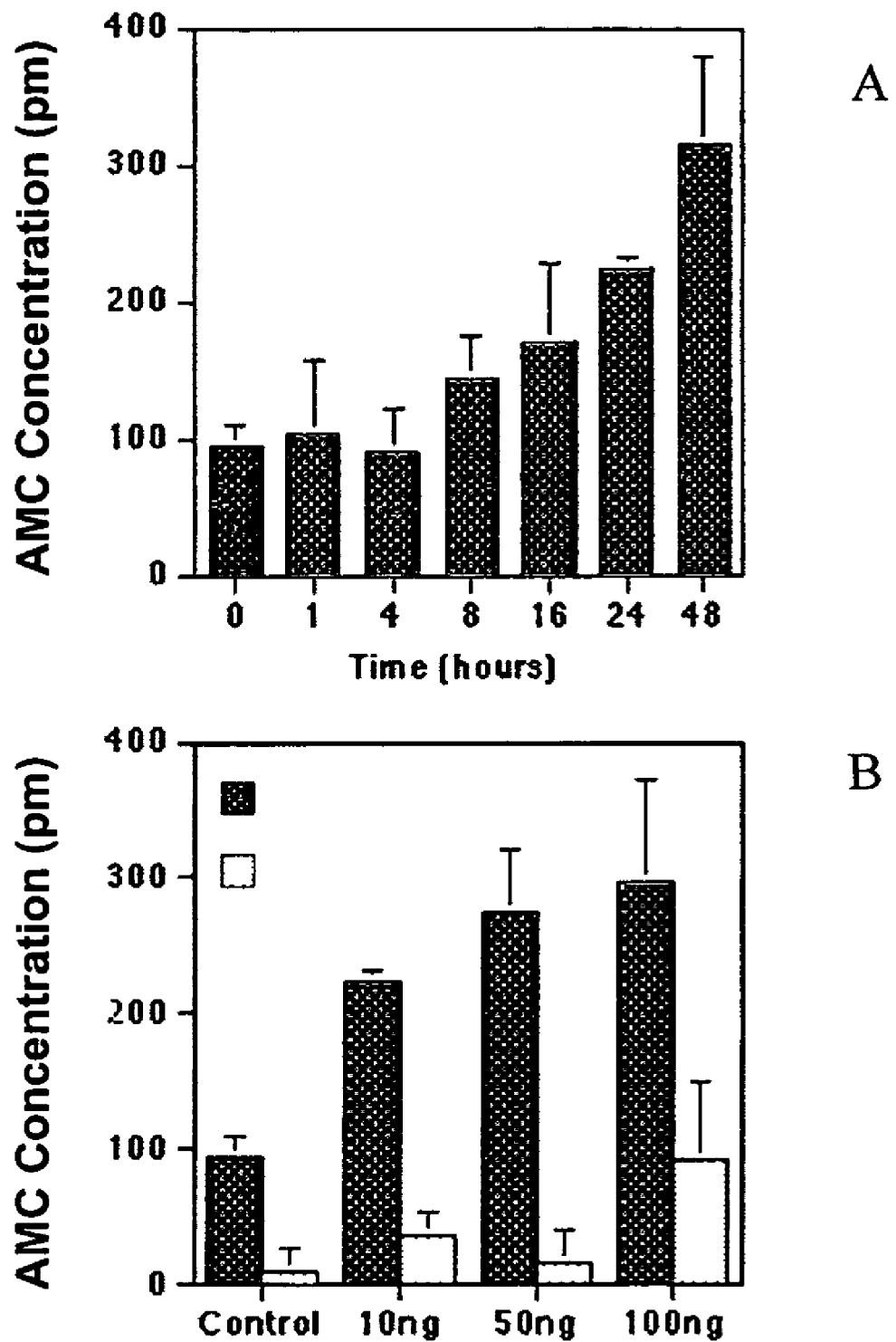
FIGS. 6A-B are bar graphs showing paclitaxel-mediated calpain activation in PC12 cells. Panel A shows time-dependent increase in calpain activity in response to 10 ng/ml paclitaxel. Panel B shows dose-dependent calpain activation at 24 hours. Calpain activation is suppressed by addition of 50 µM AK295. AMC concentration is a direct measure of calpain activity.
Figure 7:
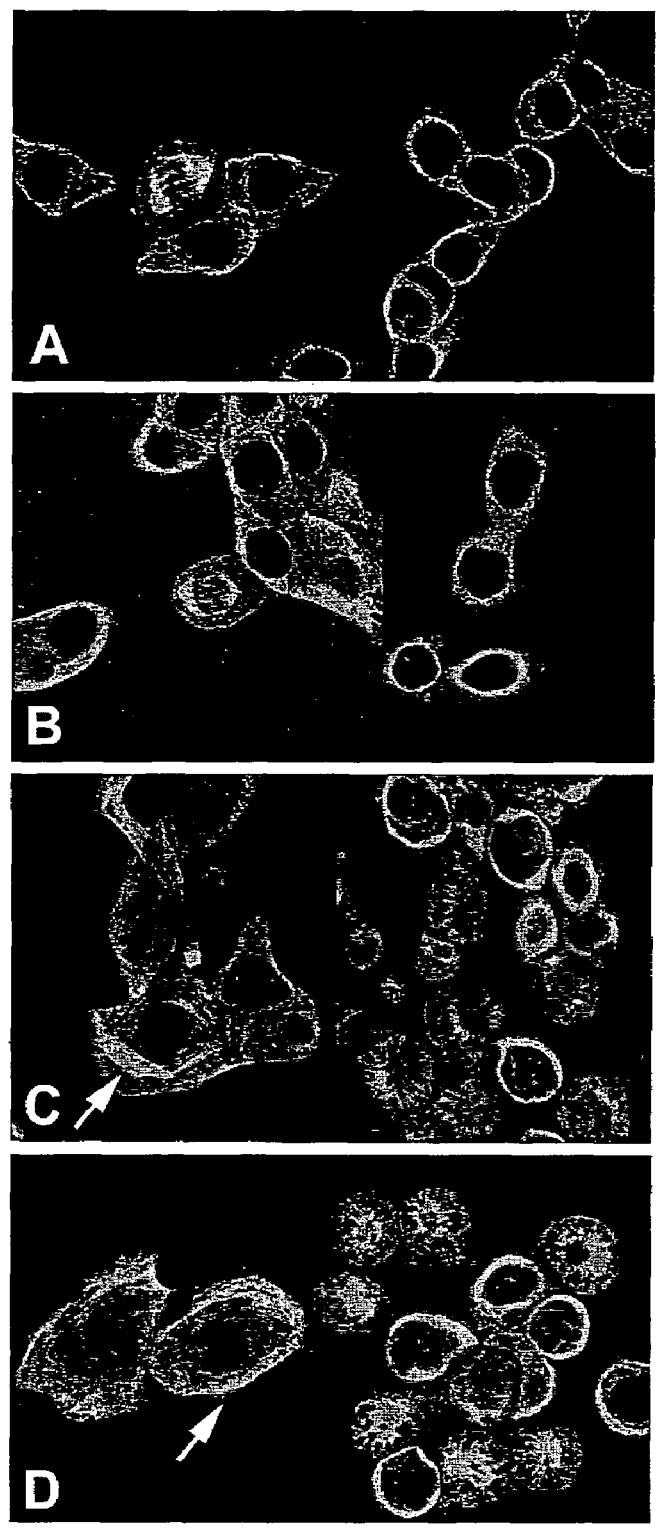
FIGS. 7A-D are confocal images of PC12 cells stained with antibody to α-tublin. Panel A shows untreated (control) cells with delicate microtubule structures with only occasional mitotic elements. Panel B shows the addition of 50 µM AK295 to PC12 cells has little or no effect. Panel C show cells 24 hours after treatment with paclitaxel (300 ng/ml). Microtubules are bundled (arrow) and there are frequent mitotic elements, indicating mitotic arrest. Panel D shows AK295 has no effect on tubulin bundling or mitotic arrest on PC12 cells treated with paclitaxel.

PC12 cells were used to demonstrate that exposure to paclitaxel can induce calpain activation and that AK295 inhibits calpain activity. In PC12 cells there was both time and dose-dependent increase in calpain activity as measured by cleavage of a synthetic calpain substrate (FIGS. 6A-B). AK295 inhibited calpain-mediated cleavage of the substrate. It is of interest to note that AK295 reduced the baseline calpain activity measured in non-treated cells as well, without causing any apparent toxicity.

Example 4

Paclitaxel-induced Tubulin Aggregation and Cell Death

Figure 8:
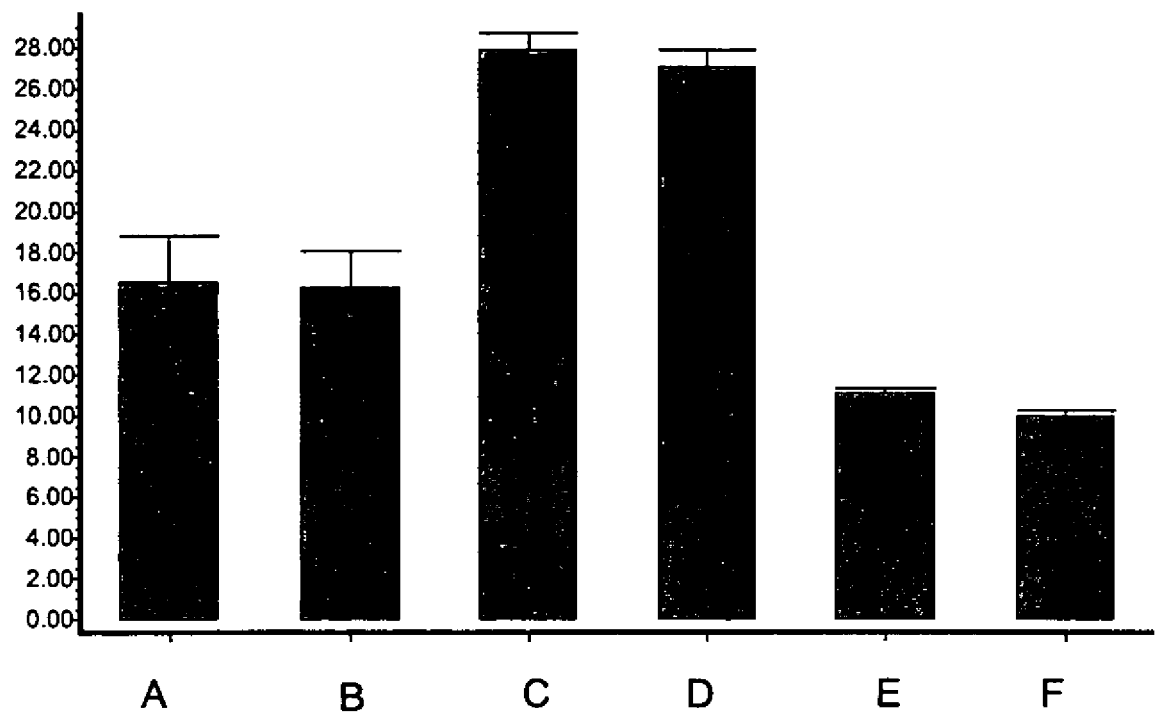
FIG. 8 is a bar graph showing results of a Sytox® assay for cell death in PC12 cells 24 hours after addition of paclitaxel (100 ng/ml). Higher fluorescence correlates with increased cell death. A) control; B) AK295 only; C) paclitaxel 100 ng/ml; D) paclitaxel 100 ng/ml and AK295 50 µM; E) paclitaxel 100 ng/ml and JG36 (caspase-3 inhibitor) 50 µM; F) JG36 only.

The antineoplastic effects of paclitaxel are based on its capacity to bind and stabilize microtubules, leading to mitotic arrest, activation of caspases and cell death. We were concerned that inhibition of calpains with AK295 might interfere with Paclitaxel-mediated cell death. To address this issue we used PC12 cells to assess the effect of AK295 on the formation of tubulin bundles and caspase-mediated cell death in response to paclitaxel exposure. PC12 cells showed aggregation of α-tubulin after exposure to paclitaxel with or without addition of AK295 (FIGS. 7A-D). The frequency of mitotic arrest was also unchanged in cells treated with AK295. The Sytox® cytotoxicity assay showed cell death after exposure to paclitaxel that was unaffected by the presence of AK295 (FIG. 8). Addition of a caspase-3 inhibitor reduced cell death to control levels.

Example 5

Calpain Inhibition with AK295 in a Model of Diabetic Neuropathy

Figure 9:
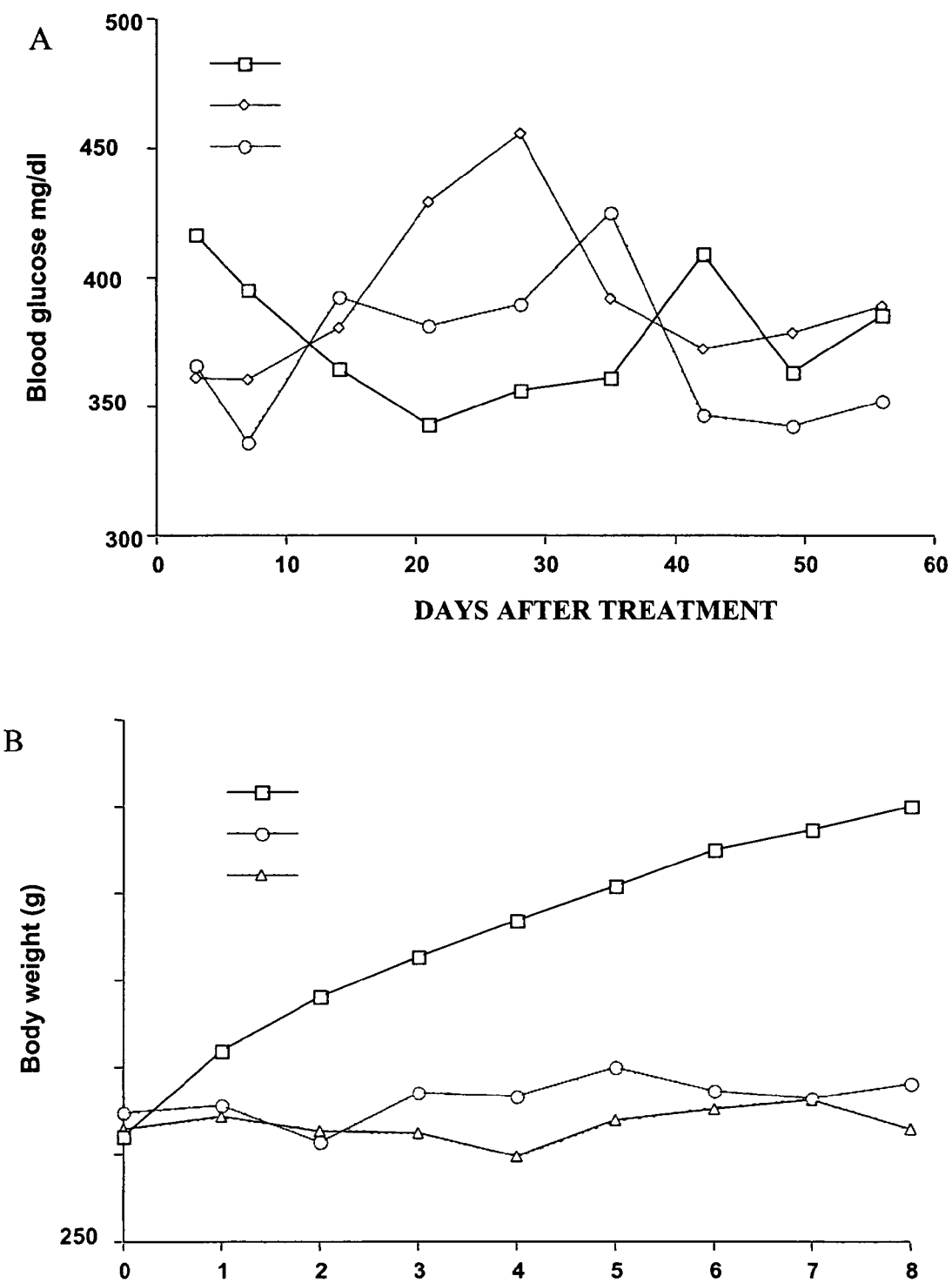
FIGS. 9A-B are line graphs showing clinical characteristics of rats with STZ diabetes.
Figure 10:
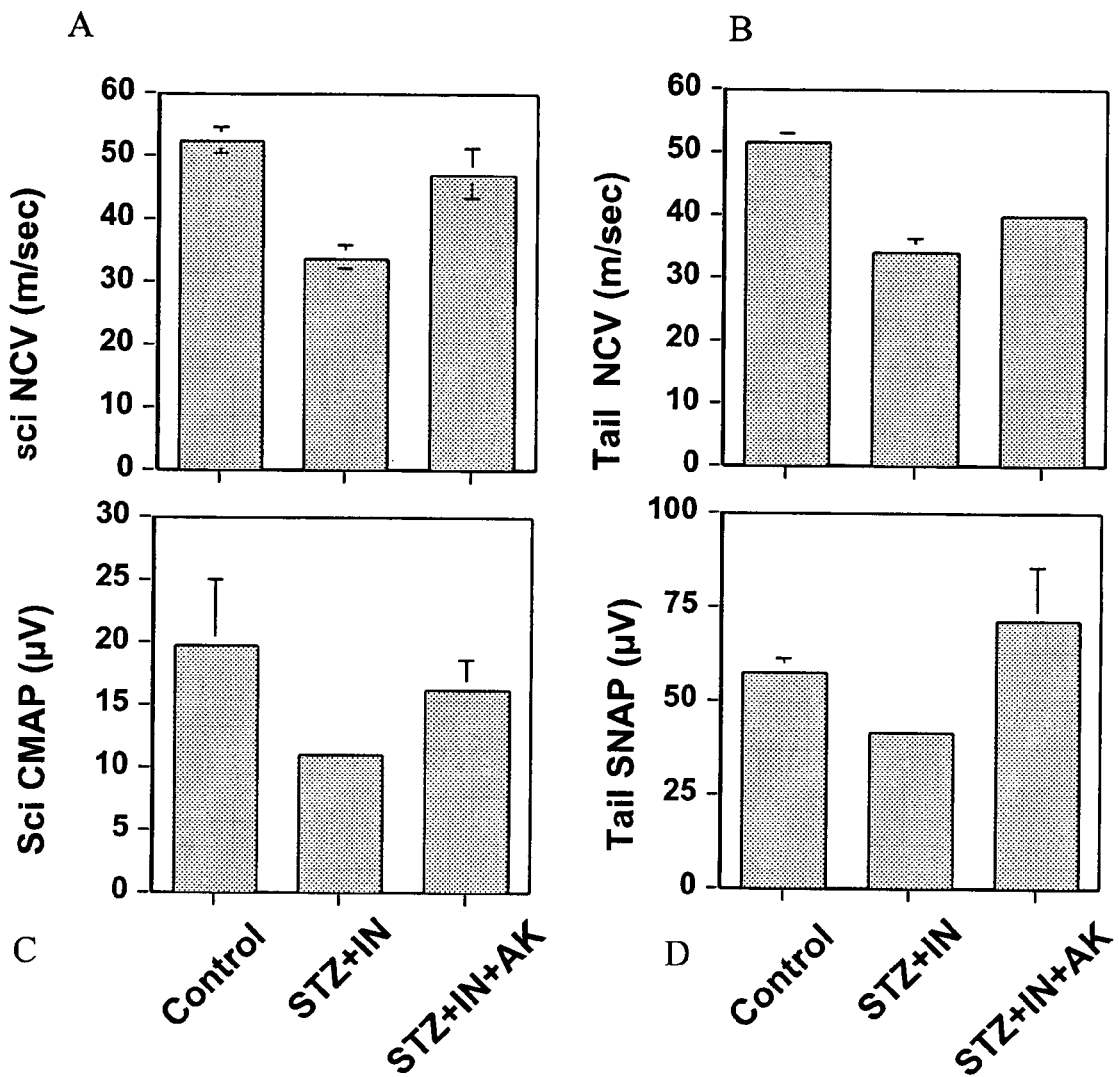
FIGS. 10A-D are bar graphs showing AK295 protects against diabetes-induced slowing of nerve conduction velocity and action potential amplitude. Data and p-values in chart. Sci=sciatic, CMAP=compound muscle action potential, SNAP=sensory nerve action potential amplitude, STZ=streptozotocin, IN=insulin treated, AK=AK295 treated.
Figure 11:
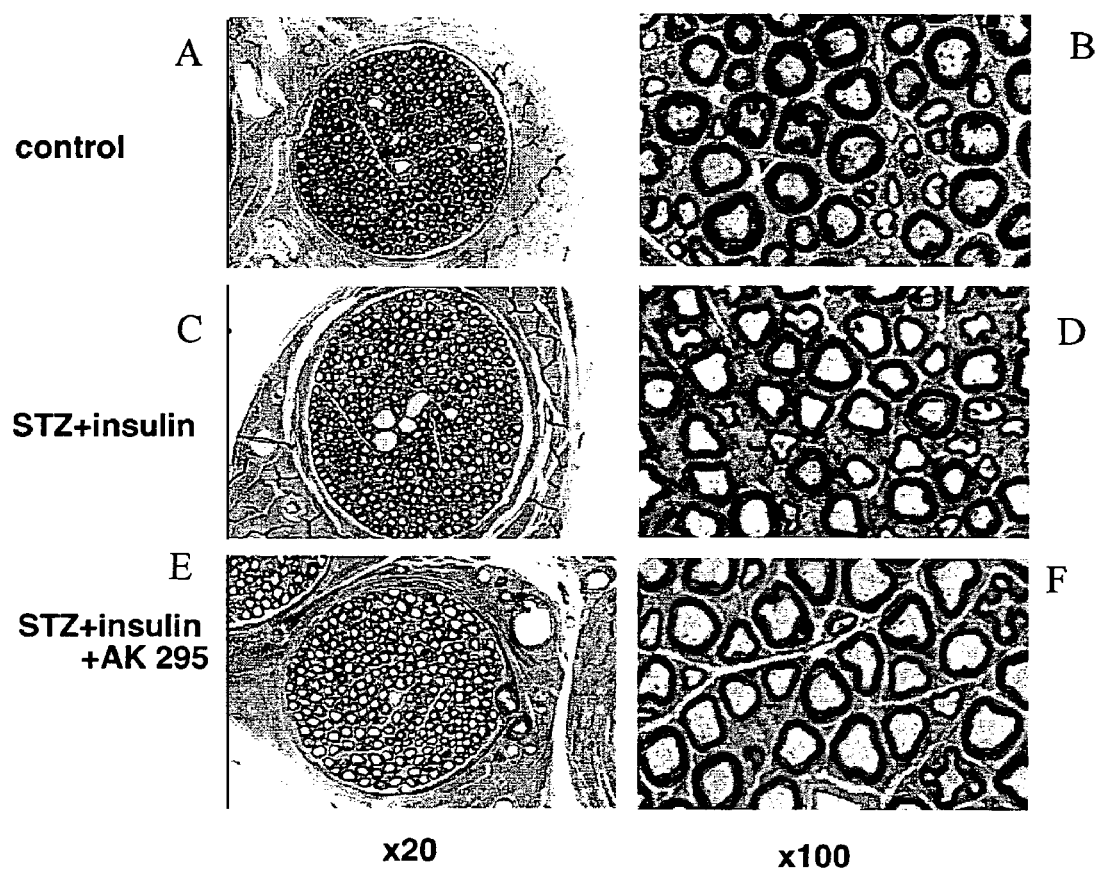
FIGS. 11A-F are photomicrographs showing morphology and morphometry of sural nerve 8 weeks after treatment. There is little morphologic evidence of axonal degeneration, but morphometry demonstrates that AK295 protects against axonal atrophy. There is a trend toward more axons in the AK295 treated group.
Figure 12:
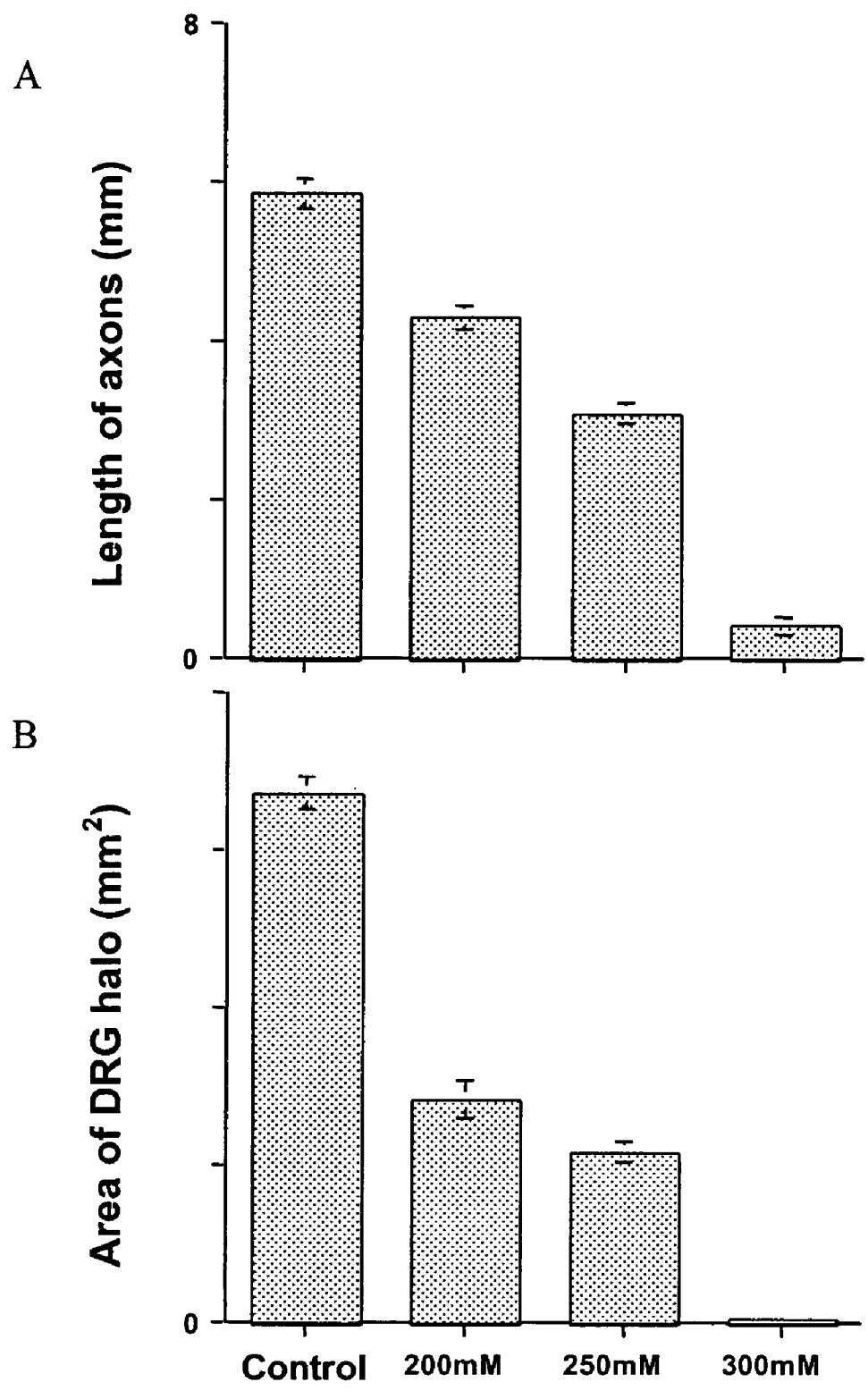
FIGS. 12A and 12B are bar graphs showing dose dependent axonal degeneration in response to increasing levels of glucose.
Figure 13:
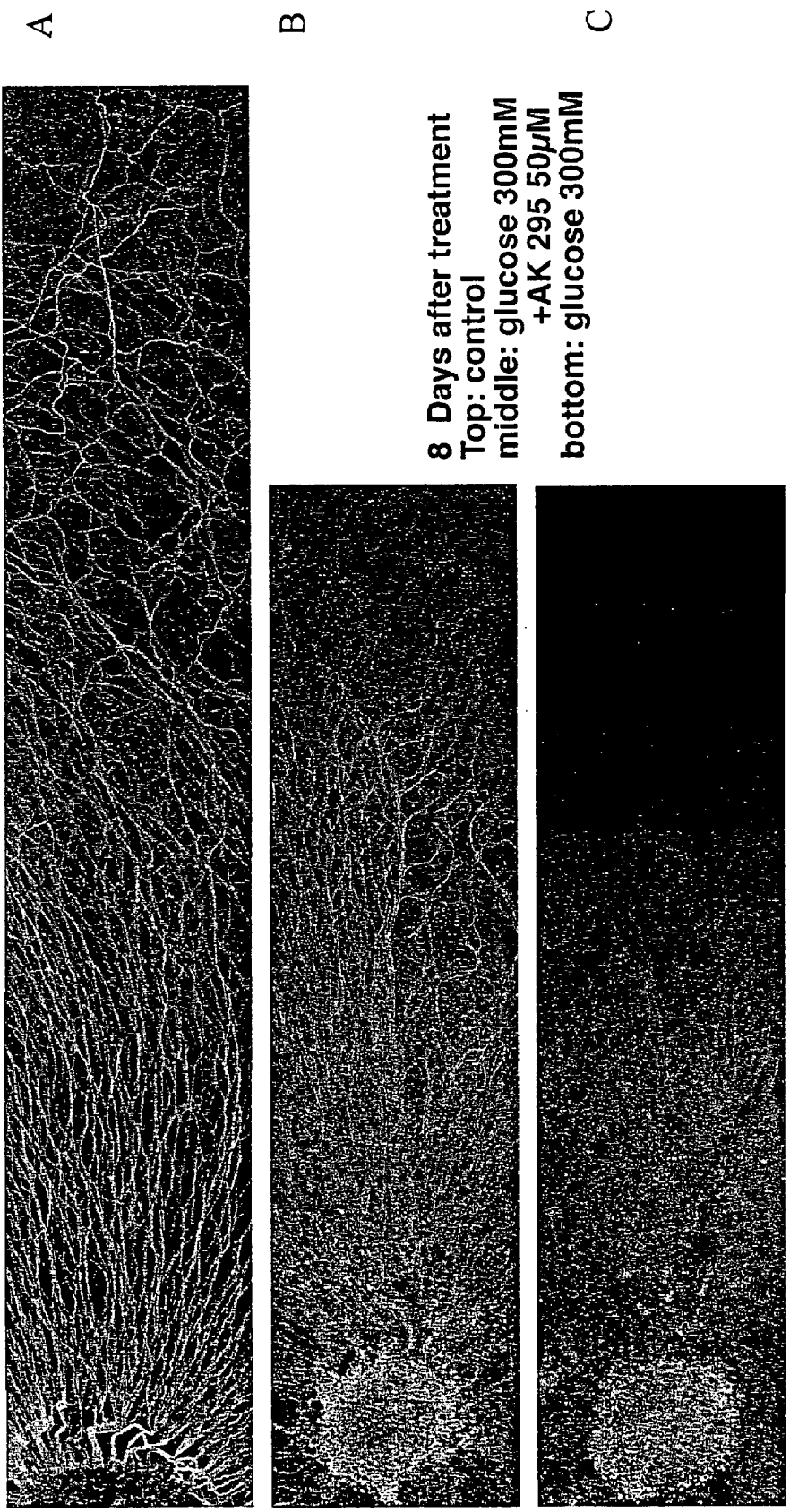
FIGS. 13A-C are fluorescence photomicrographs of DRG cultures treated with glucose only (panel C) or glucose with AK295 (panel B). Panel A is the normal control showing the expected growth of axons over the experimental time period. Note the relative preservation of axons in the AK295 treated culture. Cultures treated for 8 days with 200 mM glucose, fixed and stained with MAP-5 axonal marker.

AK295 was tested for its ability to modify the clinical and pathological features of diabetes mellitus-related peripheral neuropathy. Wistar rats (male, 9 weeks old) were treated with a single dose (75 mg/kg iv) of the pancreatic toxin streptozotocin (STZ), causing them to become diabetic (FIGS. 9A-B). This was an 8-week study with 4 groups: 1) control (no STZ), 2) STZ only, 3) STZ+Insulin, 4) STZ+Insulin+AK295 (FIGS. 10A-D, FIGS. 11A-F, and Tables 2 and 3). Insulin was given 2x/week based on the measurement of serum glucose at a dose of 8μ/100 mg/dl. AK295 as provided as a continuous subcutaneous infusion via pump at a dose of 20 mg/kg/day based on a 300 gram rat.

Cultured DRG from E15 rats were also exposed to various levels of glucose in order to test the protection of AK295 against axonal degeneration due to glucose toxicity (FIGS. 12A-B and FIGS. 13A-C).

Figure 14:
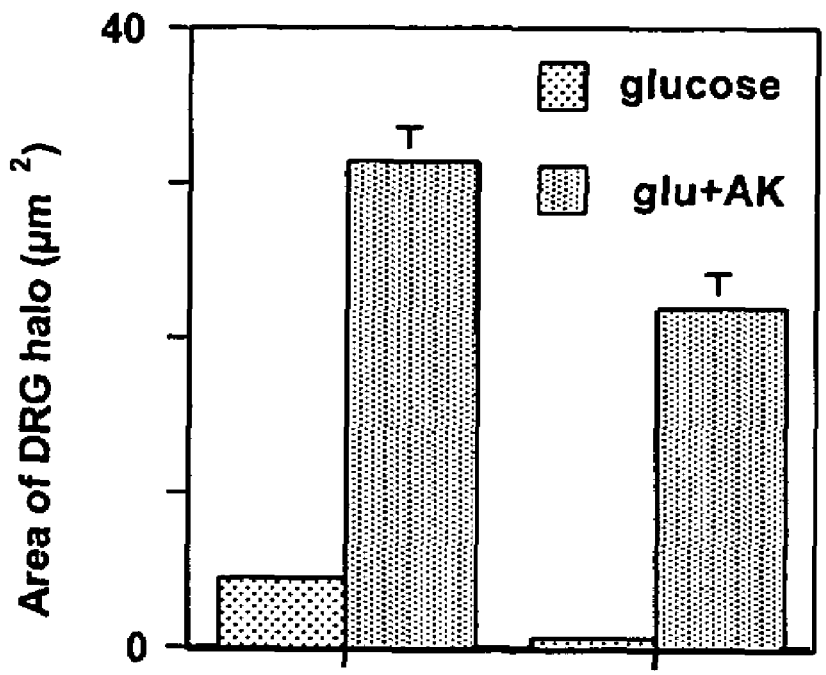
FIGS. 14A and B are bar graphs showing quantitative measure of relative protection of AK295 against high glucose-induced axonal degeneration at both 3 and 8 days after exposure.
Figure 14:
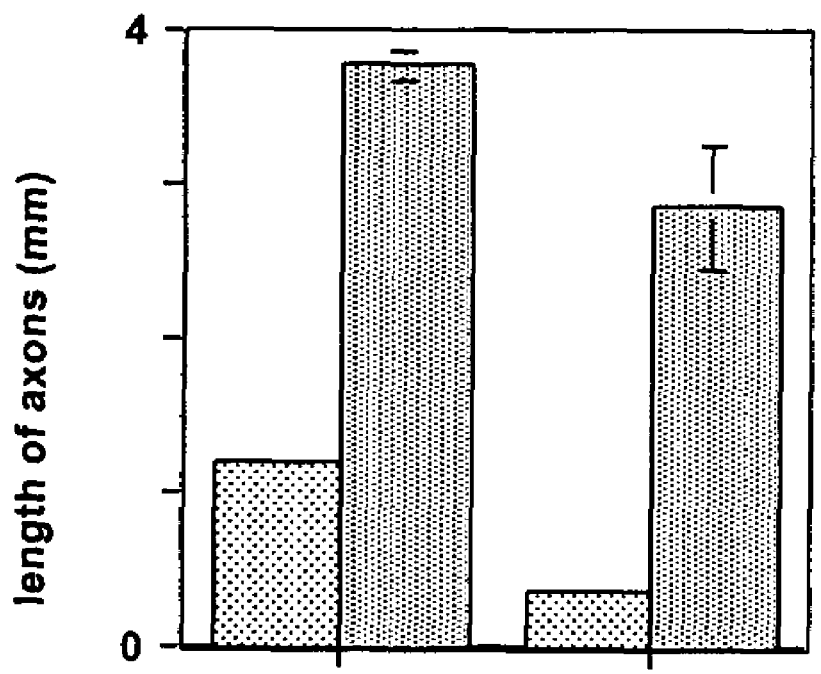

In these whole animal and cell culture models of diabetes-related neuropathy we show that there is protection by AK295 against measures of nerve function (conduction velocity and nerve amplitude), and protection against axonal degeneration (FIGS. 14A-B).

TABLE 2

| treatment | Sci CMAP | Sci NCV | Tail SNAP | Tail NCV |
|---|---|---|---|---|
| control | 19.88 ± 5.20 | 52.33 ± 2.19 | 57.64 ± 3.39* | 51.67 ± 1.45 |
| STZ | 20.43 ± 7.92 | 33.00 ± 4.04 | 37.61 ± 11.05 | 32.00 ± 2.08 |
| STZ + insulin | 10.99 ± 0.40 | 33.67 ± 1.76 | 41.52 ± 0.46 | 34.33 ± 1.86 |
| STX + insulin + AK | 16.32 ± 2.34 | 47.00 ± 4.04 | 71.33 ± 14.39 | 40.00 ± 1.00 |
| P-value (T test, AK vs. no AK) | 0.04 | 0.04 | 0.005 | 0.028 |

TABLE 3

Morphometric analysis of sural nerve after 8 weeks treatment

| group | diameter (μm) | area (μm²) | # of axons |
|---|---|---|---|
| control | 3.81 ± 0.09 | 11.74 ± 0.65 | 668 ± 65 |
| STZ + insulin | 3.57 ± 0.042* | 10.37 ± 0.19* | 680 ± 19 |
| STZ + Insulin + AK | 4.07 ± 0.097* | 13.72 ± 0.65* | 738 ± 70 |
| p value | *0.0044 | *0.004 | |

The following table lists inhibition data for calpain I and calpain II for the α-ketoamides $M^1$-Leu$^1$-AA-CONH—$R^2$. Inhibition of calpain correlates with potency in the above animal and cell based models. The following values are inhibitory potency ($K_I$) values in micromolar. Inhibitors with lower numbers are more potent.

TABLE 4

Calpain Inhibition Data

| M¹ | AA¹ | R² | Cal I | Cal II |
|---|---|---|---|---|
| Z | Nva | CH₂-2-pyridyl | 0.019 | 0.12 |
| Z | Abu | CH₂CH(OH)C₆F₅ | 0.05 | 0.2 |
| Z | Phe | (CH₂)₂Ph | 0.052 | 0.024 |
| Z | Abu | CH₂CH(OH)C₆H₄-3-OC₆H₄(3-CF₃) | 0.07 | 0.28 |
| Z | Abu | CH₂CH(OH)C₆H₄(4-OCH₂Ph) | 0.08 | 0.12 |
| Z | Abu | CH₂CH(OH)C₆H₄(4-OPh) | 0.1 | 0.29 |
| Z | Phe | CH₂-2-quinolinyl | 0.11 | 0.023 |
| Z | Abu | (CH₂)₂C₆H₄(3-OCH3) | 0.11 | 0.086 |
| Z | Abu | (CH₂)₂C₆H₄(4-OCH3) | 0.12 | 0.046 |
| Z | Abu | CH₂CH(OH)-1-C₁₀H₇ | 0.12 | 0.17 |
| Z | Phe | (CH₂)₃-4-morpholinyl | 0.12 | 0.33 |
| Z | Abu | (CH₂)₂C₆H₄(2-OCH₃) | 0.13 | 0.16 |
| Z | Abu | CH₂-2-quinolinyl | 0.13 | 0.6 |
| Z | Abu | (CH₂)₃-4-morpholinyl (AK295) | 0.14 | 0.041 |
| Z | Abu | (CH₂)₂-2-(N-methylpyrrole) | 0.16 | 0.076 |
| Z | Phe | CH₂CH(OH)C₆H₄-3-OC₆H₄(3-CF₃▫) | 0.18 | 0.45 |
| Z | Abu | (CH₂)₂C₆H₅ | 0.2 | 0.022 |
| Z | Phe | Et | 0.2 | 0.039 |
| Z | Abu | CH₂CH(OC₂H₅)₂ | 0.2 | 0.16 |
| Z | Phe | CH₂CH(OH)C₆H₄(4-OPh) | 0.2 | 0.17 |
| Z | Phe | CH₂CH(OH)C₆H₄(4-OCH₂Ph) | 0.2 | 0.24 |
| Z | Abu | CH₂C₆H₅ | 0.2 | 0.35 |
| Z | Phe | (CH₂)₂NH-biotinyl | 0.22 | 0.16 |
| Z | Phe | (CH₂)₃-2-tetrahydroisoquinolinyl | 0.22 | 0.2 |
| Z | Abu | CH₂CH(OH)C₆H₃(3,4-(OCH₂Ph)₂) | 0.23 | 0.1 |
| Z | Abu | CH₂CH(OH)C₆H₄(4-OCH₃) | 0.24 | nldpf |
| Z | Nva | (CH₂)₃-4-morpholinyl | 0.25 | 0.1 |

TABLE 4-continued

Calpain Inhibition Data

| $M^1$ | $AA^1$ | $R^2$ | Cal I | Cal II |
|---|---|---|---|---|
| Z | Abu | $CH_2$-1-isoquinolinyl | 0.25 | 0.15 |
| Z | Abu | Et | 0.25 | 0.21 |
| Z | Abu | $CH_2CH(OH)C_6H_4$-3-$OC_6H_3$(3,4-$Cl_2$) | 0.27 | 0.12 |
| Z | Abu | Me | 0.28 | 0.083 |
| Z | Abu | $(CH_2)_3$-1-imidazolyl | 0.29 | 0.068 |
| Z | Abu | $(CH_2)_2$-3-indolyl | 0.3 | 0.05 |
| Z | Abu | $(CH_2)_3$-2-tetrahydroisoquinolinyl | 0.31 | 0.19 |
| Z | Abu | $CH_2$-2-tetrahydrofuryl | 0.33 | 0.066 |
| Z | Abu | $CH_2CH(OH)C_6H_4$(4-$N(CH_3)_2$) | 0.33 | 0.41 |
| Z | Phe | n-Pr | 0.35 | 0.05 |
| Z | Abu | $CH_2CH(OH)$-2-$C_{10}H_7$ | 0.35 | 0.11 |
| Z | Phe | Me | 0.35 | 0.15 |
| Z | Abu | $CH_2CH(OH)C_6H_4$(3-$CF_3$) | 0.35 | 0.18 |
| Z | Abu | $(CH_2)_3$-1-tetrahydroquinolinyl | 0.37 | 0.2 |
| Z | Abu | $(CH_2)_2C_6H_4$(4-OH) | 0.38 | 0.06 |
| Z | Abu | $CH_2CH(OH)C_6H_2$(3,4,5-$(OCH_3)_3$) | 0.38 | 0.22 |
| Z | Phe | $(CH_2)_3$-1-tetrahydroquinolinyl | 0.38 | 0.26 |
| Z | Abu | $(CH_2)_3$-2-pyridyl | 0.41 | 0.47 |
| Z | Abu | $CH_2$—$C_6H_7$(1,3,3-$(CH_3)_3$-5-OH) | 0.42 | 0.069 |
| Z | Phe | $CH_2CH(OH)C_6H_4$(3-CF3) | 0.46 | 0.29 |
| Z | Phe | $CH_2CH(OH)C_6H_3$(3,4-$(OCH_2Ph)_2$) | 0.48 | 0.67 |
| Z | Abu | $(CH_2)_5OH$ | 0.5 | 0.051 |
| Z | Abu | $CH_2CH(OCH_3)_2$ | 0.5 | 0.1 |
| Z | Phe | $CH_2CH(OH)C_6H_4$-3-$OC_6H_3$(3,4-$Cl_2$) | 0.59 | 0.12 |
| Z | Phe | $CH_2CH(OH)C_6H_4$(3-OPh) | 0.6 | 0.34 |
| Z | Phe | $CH_2CH(OH)C_6H_4$(4-$N(CH_3)_2$) | 0.62 | 0.31 |
| Z | Abu | $CH_2$-2-pyridyl | 0.64 | 0.017 |
| Z | Abu | $(CH_2)_2O(CH_2)_2OH$ | 0.65 | 0.16 |
| Z | Phe | $CH_2$-2-pyridyl | 0.65 | 0.27 |
| Z | Abu | $(CH_2)_2$NH-biotinyl | 0.65 | 0.28 |
| Z | Abu | $CH_2$—$C_6H_{11}$ | 0.68 | 0.044 |
| Z | Phe | $CH_2CH(OH)C_6F_5$ | 0.7 | 0.35 |
| Z | Abu | $CH_2$-2-furyl | 0.8 | 0.033 |
| Z | Abu | $(CH_2)_3C_6H_5$ | 0.8 | 0.043 |
| Z | Abu | $(CH_2)_2OH$ | 0.8 | 0.078 |
| Z | Abu | $CH_2CH(OH)C_6H_4$(3-OPh) | 0.9 | 0.59 |
| Z | Abu | $(CH_2)_2$-4-morpholinyl | 1 | 0.16 |
| Z | Abu | $CH_2CH(OH)Ph$ | 1.1 | 0.015 |
| Z | Abu | $CH_2$-4-pyridyl | 1.1 | 0.11 |
| Z | Abu | $(CH_2)_3$-1-pyrrolidine-2-one | 1.2 | 0.27 |
| Z | Phe | $CH_2CH(OH)Ph$ | 1.3 | 0.05 |
| Z | Abu | $CH_2C_6H_3$(3,5-$(OCH_3)_2$) | 2.3 | 0.022 |
| Z | Nva | $CH_2CH(OH)Ph$ | 7.8 | 11 |
| Z | Abu | $CH_2$-8-caffeinyl | 32 | 4.6 |
| Z | Abu | n-Pr |  | 0.25 |
| Z | Abu | $CH_2$-3-pyridyl |  | 0.12 |
| Z | Phe | $CH_2Ph$ |  | 0.046 |

Axonal degeneration is a feature common to a wide spectrum of neurologic disorders and axonal degeneration is the pathology that underlies clinical dysfunction in these disorders. These diseases include, peripheral neuropathies due to genetic mutations, peripheral neuropathies associated with other systemic diseases including uremia, rheumatologic diseases, liver diseases, and infections, axonal degeneration secondary to primary demyelinating disorders including inflammatory demyelinating neuropathies and multiple sclerosis. These α-ketoamide calpain inhibitors will be effective in preventing axonal degeneration in these other disorders and will thus constitute a novel treatment for these diseases.

The above specification and Examples fully disclose how to make and use the methods of the present invention. However, the present invention is not limited to the particular embodiments described herein, but includes all modifications thereof within the scope of the following claims. The various references to journals, patents, and other publications which are cited herein comprise the state of the art and are incorporated herein by reference.

What is claimed is:
1. A method for treating axonal degeneration of the peripheral nervous system of a patient comprising administering to the patient a compound selected from the group consisting of:
Z-Leu-Nva-CO—NH—$CH_2$-2-pyridyl,
Z-Leu-Abu-CO—NH—$CH_2CH(OH)C_6F_5$,
Z-Leu-Phe-CO—NH—$(CH_2)_2Ph$,
Z-Leu-Abu-CO—NH—$CH_2CH(OH)C_6H_4$-3-$OC_6H_4$(3-$CF_3$),
Z-Leu-Abu-CO—NH—$CH_2CH(OH)C_6H_4$(4-$OCH_2Ph$),
Z-Leu-Abu-CO—NH—$CH_2CH(OH)C_6H_4$(4-OPh),
Z-Leu-Phe-CO—NH—$CH_2$-2-quinolinyl,
Z-Leu-Abu-CO—NH—$(CH_2)_2C_6H_4$(3-$OCH_3$),
Z-Leu-Abu-CO—NH—$(CH_2)_2C_6H_4$(4-$OCH_3$),
Z-Leu-Abu-CO—NH—$CH_2CH(OH)$-1-$C_{10}H_7$,
Z-Leu-Phe-CO—NH—$(CH_2)_3$-4-morpholinyl,
Z-Leu-Abu-CO—NH—$(CH_2)_2C_6H_4$(2-$OCH_3$),
Z-Leu-Abu-CO—NH—$CH_2$-2-quinolinyl,
Z-Leu-Abu-CO—NH—$(CH_2)_2$-2-(N-methylpyrrole),
Z-Leu-Phe-CO—NH—$CH_2CH(OH)C_6H_4$-3-$OC_6H_4$(3-$CF_3$),
Z-Leu-Abu-CO—NH—$(CH_2)_2C_6H_5$,
Z-Leu-Phe-CO—NH-Et,
Z-Leu-Abu-CO—NH—$CH_2CH(OC_2H_5)_2$,
Z-Leu-Phe-CO—NH—$CH_2CH(OH)C_6H_4$(4-OPh),
Z-Leu-Phe-CO—NH—$CH_2CH(OH)C_6H_4$(4-$OCH_2Ph$),
Z-Leu-Abu-CO—NH—$CH_2C_6H_5$,
Z-Leu-Phe-CO—NH—$(CH_2)_2$NH-biotinyl,
Z-Leu-Phe-CO—NH—$(CH_2)_3$-2-tetrahydroisoquinolinyl,
Z-Leu-Abu-CO—NH—$CH_2CH(OH)C_6H_3$(3,4-$(OCH_2Ph)_2$),
Z-Leu-Abu-CO—NH—$CH_2CH(OH)C_6H_4$(4-$OCH_3$),
Z-Leu-Nva-CO—NH—$(CH_2)_3$-4-morpholinyl,
Z-Leu-Abu-CO—NH—$CH_2$-1-isoquinolinyl,
Z-Leu-Abu-CO—NH-Et,
Z-Leu-Abu-CO—NH—$CH_2CH(OH)C_6H_4$-3-$OC_6H_3$(3,4-$Cl_2$),
Z-Leu-Abu-CO—NH-Me,
Z-Leu-Abu-CO—NH—$(CH_2)_3$-1-imidazolyl,
Z-Leu-Abu-CO—NH—$(CH_2)_2$-3-indolyl,
Z-Leu-Abu-CO—NH—$(CH_2)_3$-2-tetrahydroisoquinolinyl,
Z-Leu-Abu-CO—NH—$CH_2$-2-tetrahydrofuryl,
Z-Leu-Abu-CO—NH—$CH_2CH(OH)C_6H_4$(4-$N(CH_3)_2$),
Z-Leu-Phe-CO—NH-n-Pr,
Z-Leu-Abu-CO—NH—$CH_2CH(OH)$-2-$C_{10}H_7$,
Z-Leu-Phe-CO—NH-Me,
Z-Leu-Abu-CO—NH—$CH_2CH(OH)C_6H_4$(3-$CF_3$),
Z-Leu-Abu-CO—NH—$(CH_2)_3$-1-tetrahydroquinolinyl,
Z-Leu-Abu-CO—NH—$(CH_2)_2C_6H_4$(4-OH),
Z-Leu-Abu-CO—NH—$CH_2CH(OH)C_6H_2$(3,4,5-$(OCH_3)_3$),
Z-Leu-Phe-CO—NH—$(CH_2)_3$-1-tetrahydroquinolinyl,
Z-Leu-Abu-CO—NH—$(CH_2)_2$-2-pyridyl,
Z-Leu-Abu-CO—NH—$CH_2$-$C_6H_7$(1,3,3-$(CH_3)_3$-5-OH),
Z-Leu-Phe-CO—NH—$CH_2CH(OH)C_6H_4$(3-$CF_3$),
Z-Leu-Phe-CO—NH—$CH_2CH(OH)C_6H_3$(3,4-$(OCH_2Ph)_2$),
Z-Leu-Abu-CO—NH—$(CH_2)_5OH$,
Z-Leu-Abu-CO—NH—$CH_2CH(OCH_3)_2$,
Z-Leu-Phe-CO—NH—$CH_2CH(OH)C_6H_4$-3-$OC_6H_3$(3,4-$Cl_2$),
Z-Leu-Phe-CO—NH—$CH_2CH(OH)C_6H_4$(3-OPh),
Z-Leu-Phe-CO—NH—$CH_2CH(OH)C_6H_4$(4-$N(CH_3)_2$),
Z-Leu-Abu-CO—NH—$CH_2$-2-pyridyl,
Z-Leu-Abu-CO—NH—$(CH_2)_2O(CH_2)_2OH$,

Z-Leu-Phe-CO—NH—CH$_2$-2-pyridyl,
Z-Leu-Abu-CO—NH—(CH$_2$)$_2$NH-biotinyl,
Z-Leu-Abu-CO—NH—CH$_2$—C$_6$H$_{11}$,
Z-Leu-Phe-CO—NH—CH$_2$CH(OH)C$_6$F$_5$,
Z-Leu-Abu-CO—NH—CH$_2$-2-furyl,
Z-Leu-Abu-CO—NH—(CH$_2$)$_3$C$_6$H$_5$,
Z-Leu-Abu-CO—NH—(CH$_2$)$_2$OH,
Z-Leu-Abu-CO—NH—CH$_2$CH(OH)C$_6$H$_4$(3-OPh),
Z-Leu-Abu-CO—NH—(CH$_2$)$_2$-4-morpholinyl,
Z-Leu-Abu-CO—NH—CH$_2$CH(OH)Ph,
Z-Leu-Abu-CO—NH—CH$_2$-4-pyridyl,
Z-Leu-Abu-CO—NH—(CH$_2$)$_3$-1-pyrrolidine-2-one,
Z-Leu-Phe-CO—NH—CH$_2$CH(OH)Ph,
Z-Leu-Abu-CO—NH—CH$_2$C$_6$H$_3$(3,5-(OCH$_3$)$_2$),
Z-Leu-Nva-CO—NH—CH$_2$CH(OH)Ph,
Z-Leu-Abu-CO—NH—CH$_2$-8-caffeinyl,
Z-Leu-Abu-CO—NH-n-Pr,
Z-Leu-Abu-CO—NH—CH$_2$-3-pyridyl,
Z-Leu-Phe-CO—NH—CH$_2$Ph, and
Z-Leu-Abu-CONH—(CH$_2$)$_3$-4-morpholinyl;
wherein Z is a benzyloxycarbonyl group.

2. The method of claim 1, wherein the compound is Z-Leu-Abu-CONH—(CH$_2$)$_3$-4-morpholinyl.

3. The method of claim 1, wherein the axonal degeneration of the peripheral nervous system is chemically-induced axonal degeneration.

4. The method of claim 1, wherein the compound is administered concurrently with an anti-hyperproliferative agent.

5. The method of claim 1, wherein the compound is administered subsequent to administration of an anti-hyperproliferative agent.

6. The method of claim 1, wherein the compound is administered orally.

* * * * *